United States Patent [19]

Olson

[11] Patent Number: 5,219,856
[45] Date of Patent: Jun. 15, 1993

[54] ANGIOTENSIN-II RECEPTOR BLOCKING, HETEROCYCLE SUBSTITUTED IMIDAZOLES

[75] Inventor: Richard E. Olson, Wilmington, Del.

[73] Assignee: E. I. du Pont de Nemours and Company, Wilmington, Del.

[21] Appl. No.: 863,881

[22] Filed: Apr. 6, 1992

[51] Int. Cl.$^5$ ............... C07D 401/14; C07D 403/14; A61K 31/495; A61K 31/535
[52] U.S. Cl. .................... 514/252; 544/364; 544/370; 544/337; 544/121; 514/85; 514/235.8
[58] Field of Search ............ 544/364, 370, 337, 121; 514/252, 85, 235.8

[56]  References Cited
   FOREIGN PATENT DOCUMENTS 0324377  7/1989  European Pat. Off. .
WO91/00277  6/1990  PCT Int'l Appl. .

Primary Examiner—Mary C. Lee
Assistant Examiner—Lenora A. Miltenberger

[57] ABSTRACT

Novel heterocycle substituted imidazoles of Formula (I), which are useful as angiotensin-II antagonists, are disclosed:

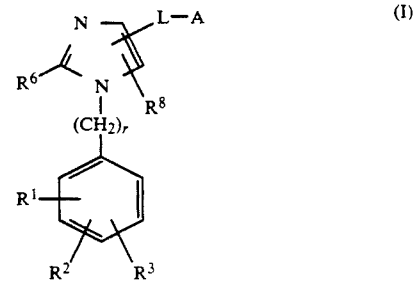

11 Claims, No Drawings

ANGIOTENSIN-II RECEPTOR BLOCKING, HETEROCYCLE SUBSTITUTED IMIDAZOLES

BACKGROUND OF THE INVENTION

1. Field of the Invention

This invention relates to novel heterocycle substituted imidazoles. The invention also relates to pharmaceutical compositions containing the novel imidazoles and pharmaceutical methods using them, alone and in conjugation with other drugs, especially diuretics, angiotensin converting enzyme (ACE) inhibitors, and non-steroidal anti-inflammatory drugs (NSAIDS).

The compounds of this invention inhibit the action of the hormone angiotensin-II (AII) and are useful therefore in alleviating angiotensin induced hypertension. The enzyme renin acts on a blood plasma α2-globulin, angiotensinogen, to produce angiotensin-I, which is then converted by ACE to AII. The latter substance is a powerful vasopressor agent which has been implicated as a causative agent for producing high blood pressure in various mammalian species, such as the rat, dog, and man. The compounds of this invention inhibit the action of AII at its receptors on target cells and thus prevent the increase in blood pressure produced by this hormone-receptor interaction. By administering a compound of this invention to a species of mammal with hypertension due to AII, the blood pressure is reduced. The compounds of this invention are also useful for the treatment of congestive heart failure. Administration of a compound of this invention with a diuretic such as furosemide or hydrochlorothiazide, either as a stepwise combined therapy (diuretic first) or as a physical mixture, enhances the antihypertensive effect of the compound. Administration of a compound of this invention with a NSAID can prevent renal failure which sometimes results from administration of a NSAID.

Several peptide analogs of AII are known to inhibit the effects of this hormone by competitively blocking the receptors, but their experimental and clinical applications have been limited by their partial agonist activity and lack of oral absorption (M. Antonaccio, *Clin. Exp. Hypertens.*, 1982, A4, 27–46; D. H. P. Streeten and G. H. Anderson, Jr.—*Handbook of Hypertension, Clinical Pharmacology of Antihypertensive Drugs*, ed., A. E. Doyle, Vol. 5, pages 246–271, Elsevier Science Publisher, Amsterdam, The Netherlands, 1984).

Several non-peptide antagonists of AII have been disclosed. Some of these compounds are covered by U.S. Pat. Nos. 4,207,324; 4,340,598; 4,576,958; 4,582,847; and 4,880,804; in European Patent Applications 028,834; 324,377; 253,310; and 291,969; and in articles by A. T. Chiu, et al. (*Eur. J. Pharm. Exp. Therap.*, 1988, 157, 13–21) and by P. C. Wong, et al. (*J. Pharm. Exp. Therap.* 1988, 247, 1–7).

These publications disclose substituted imidazole compounds which are bonded through a lower alkyl bridge to a substituted phenyl. Among the above references, European Patent Application 324,377 describes imidazoles where the imidazole ring can be substituted at the 4- or 5-position with heterocycle containing substituents, including

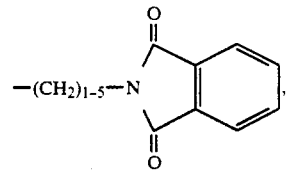

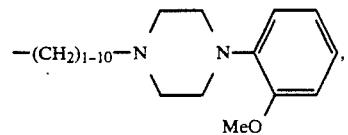

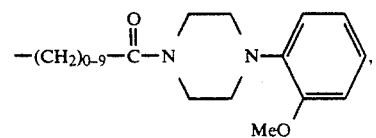

$-CH=CH(CH_2)_{0-5}COR^{16}$, $-COR^{16}$, $-(CH_2)_{0-5}-CH(CH_3)-COR^{16}$ and $-(CH_2)_{1-10}COR^{16}$, where $R^{16}$ may be

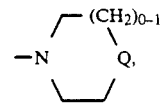

in which Q is OH, $CH_2$ or $NR^{20}$, where $R^{20}$ is H, alkyl of 1 to 4 carbon atoms or phenyl.

US90/03683 describes imidazoles having the same basic formula as EPO 0324377, where the imidazole ring can be substituted at the 4- or 5-position with heterocycle containing substituents, including alkyl, alkenyl or alkynyl of 1 to 10 carbon atoms substituted with N-phthalimido or

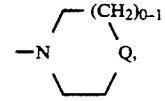

$-CH=CH(CH_2)_{0-5}COR^{16}$, $-COR^{16}$, $-(CH_2)_{0-5}-CH(CH_3)-COR^{16}$ and $-(CH_2)_{1-10}OCOR^{16}$ where $R^{16}$ is as defined in EPO 0324377.

None of the above publications disclose the novel heterocycle substituted imidazoles of the present invention.

SUMMARY OF THE INVENTION

This invention pertains to novel angiotensin-II blocking imidazole compounds of the following Formula (I):

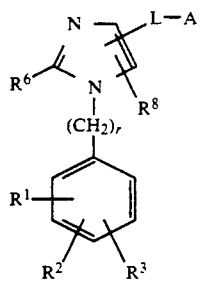

(I)

wherein
R¹ is in the meta or para position and is
  (a) 4-CO₂H,
  (b) —CH₂CO₂H,
  (c) —C(CF₃)₂OH,
  (d) —CONHNHSO₂CF₃,
  (e) 4-CONHCH(CO₂H)CH₂C₆H₅ (L-isomer),
  (f) 4-CONHOR¹²,
  (g) —CONHSO₂R¹⁰,
  (h) —CONHSO₂NHR⁹,
  (i) —C(OH)R⁹PO₃H₂,
  (j) —NHCOCF₃,
  (k) —NHCONHSO₂R¹⁰,
  (l) —NHPO₃H₂,
  (m) 4-NHSO₂R¹⁰,
  (n) —NHSO₂NHCOR¹⁰,
  (o) —OPO₃H₂,
  (p) —OSO₃H,
  (q) —PO₃H₂,
  (r) —SO₃H,
  (t) —SO₂NHR⁹,
  (u) —SO₂NHCOR¹⁰,
  (v) —SO₂NHCONHR⁹, (w) 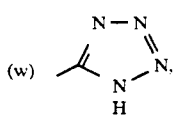

(x) 4-CONH 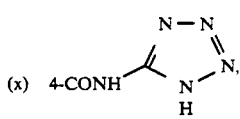

(y) 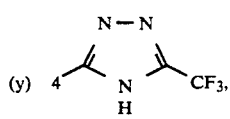

(z) 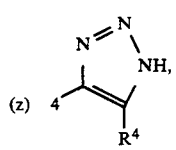

(aa) 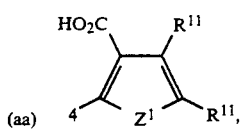

(bb) 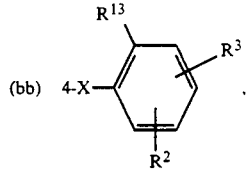

(cc) 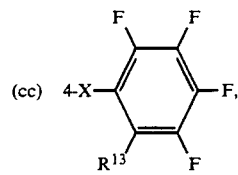

(dd) 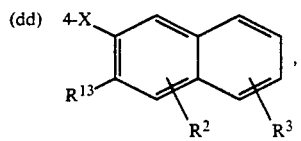

(ee) 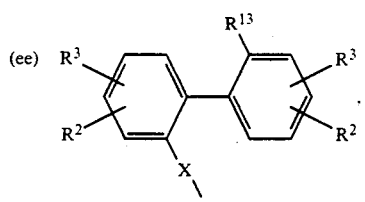

(ff) 4-N 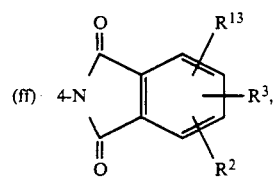

(gg) 4-X 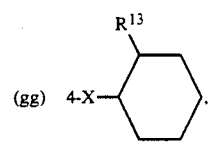

(hh) 4-CO 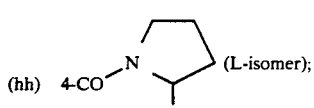 (L-isomer);

R² is independently
  (a) H,
  (b) halo (F, Cl, Br, I),
  (c) C₁-C₄ alkyl,
  (d) C₁-C₄ alkoxy,
  (e) C₁-C₄ acyloxy,
  (f) C₁-C₄ alkylthio,
  (g) C₁-C₄ alkylsulfinyl,
  (h) C₁-C₄ alkylsulfonyl,
  (i) hydroxy (C₁-C₄) alkyl,
  (j) aryl (C₁-C₄) alkyl,
  (k) —CO₂H,
  (l) —CN,
  (m) tetrazol-5-yl,
  (n) —CONHOR¹²,
  (o) —SO₂NHR⁹,
  (p) —NH₂, (q) $C_1-C_4$ alkylamino,
(r) $C_1-C_4$ dialkylamino
(s) $-NHSO_2R^{10}$,
(t) $-NO_2$,
(u) furyl,
(v) aryl;
wherein aryl is phenyl optionally substituted with one or two substituents selected from the group consisting of halo, $C_1-C_4$ alkyl, $C_1-C_4$ alkoxy, $-NO_2$, $-CF_3$, $C_1-C_4$ alkylthio, $-OH$, $-NH_2$, $C_1-C_4$ alkylamino, $C_1-C_4$ dialkylamino, $-CN$, $-CO_2H$, $-CO_2CH_3$, $-CO_2CH_2CH_3$, $-CO_2$-benzyl, acetyl;

$R^3$ is independently
(a) H,
(b) halo,
(c) $C_1-C_4$ alkyl,
(d) $C_1-C_4$ alkoxy,
(e) $C_1-C_4$ alkoxyalkyl;

$R^4$ is
(a) $-CN$,
(b) $-NO_2$,
(c) $-CO_2R^{11}$;

$R^5$ is
(a) H,
(b) $C_1-C_6$ alkyl,
(c) $C_3-C_6$ cycloalkyl,
(d) $C_2-C_4$ alkenyl,
(e) $C_2-C_4$ alkynyl;

$R^6$ is
(a) $C_1-C_{10}$ alkyl,
(b) $C_3-C_{10}$ alkenyl,
(c) $C_3-C_{10}$ alkynyl,
(d) $C_3-C_8$ cycloalkyl,
(e) $C_4-C_8$ cycloalkenyl,
(f) $C_4-C_{10}$ cycloalkylalkyl,
(g) $C_5-C_{10}$ cycloalkylalkenyl,
(h) $C_5-C_{10}$ cycloalkylalkynyl,
(i) $-(CH_2)_sZ^2(CH_2)_mR^5$,
(j) benzyl, optionally substituted on the phenyl ring with 1-2 substituents selected from the group consisting of halo, $C_1-C_4$ alkyl, $C_1-C_4$ alkoxy or $-NO_2$;

$R^8$ is
(a) H,
(b) $C_1-C_4$ alkyl,
(c) $-(CH_2)_nCHR^{34}OR^{29}$,
(d) $-COR^{35}$,
(e) $-(CH_2)_nCHR^{34}COR^{35}$,
(f) $-CR^{36}=CR^{37}COR^{35}$,
(g) $-CONHOR^{12}$;

$R^9$ is
(a) H,
(b) $C_1-C_5$ alkyl,
(c) aryl,
(d) $-CH_2$-aryl,
(e) heteroaryl;
wherein heteroaryl is an unsubstituted, monosubstituted or disubstituted 5- or 6-membered aromatic ring which can optionally contain from 1 to heteroatoms selected from the group consisting of O, N, and S and wherein the substituents are members selected from the group consisting of $-OH$, $-SH$, $C_1-C_4$ alkyl, $C_1-C_4$ alkoxy, $-CF_3$, halo, $-NO_2$, $-CO_2H$, $-CO_2CH_3$, $-CO_2$-benzyl, $-NH_2$, $C_1-C_4$ alkylamino, $C_1-C_4$ dialkylamino and aryl is as defined above;

$R^{10}$ is
(a) aryl as defined above,
(b) $C_3-C_7$ cycloalkyl,
(c) $C_1-C_4$ perfluoroalkyl,
(d) $C_1-C_4$ alkyl optionally substituted with a substituent selected from the group consisting of aryl as defined above, heteroaryl as defined above, $-OH$, $-SH$, $C_1-C_4$ alkyl, $C_1-C_4$ alkoxy, $C_1-C_4$ alkylthio, $-CF_3$, halo, $-NO_2$, $-CO_2H$, $-CO_2CH_3$, $-CO_2$-benzyl, $-NH_2$, $C_1-C_4$ alkylamino, $C_1-C_4$ dialkylamino, $-PO_3H_2$;
(e) heteroaryl as defined above;

$R^{11}$ is
(a) H,
(b) $C_1-C_6$ alkyl,
(c) $C_3-C_6$ cycloalkyl,
(d) phenyl,
(e) benzyl;

$R^{12}$ is
(a) H,
(b) methyl,
(c) benzyl;

$R^{13}$ is
(a) $-CO_2H$,
(b) $-CH_2CO_2H$,
(c) $-C(CF_3)_2OH$,
(d) $-CONHNHSO_2CF_3$,
(e) $-CONHOR^{12}$,
(f) $-CONHSO_2R^{10}$,
(g) $-CONHSO_2NHR^9$,
(h) $-C(OH)R^9PO_3H_2$,
(i) $-NHCOCF_3$,
(j) $-NHCONHSO_2R^{10}$,
(k) $-NHPO_3H_2$,
(l) $-NHSO_2R^{10}$,
(m) $-NHSO_2NHCOR^{10}$,
(n) $-OPO_3H_2$,
(o) $-OSO_3H$,
(p) $-PO(OH)R^9$,
(q) $-PO_3H_2$,
(r) $-SO_3H$,
(s) $-SO_2NHR^9$,
(t) $-SO_2NHCOR^{10}$,
(u) $-SO_2NHCONHR^9$, (v) 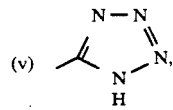

(w) $-CONH$ 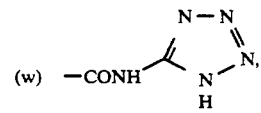

(x) 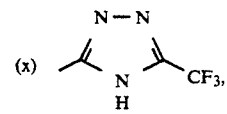

(y) 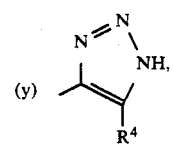

(z) 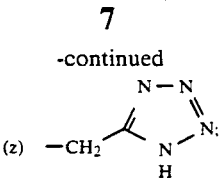

R$^{14}$ is
  (a) H,
  (b) C$_1$-C$_6$ alkyl,
  (c) CH$_2$CH=CH$_2$,
  (d) benzyl;
R$^{15}$ is
  (a) H,
  (b) C$_1$-C$_8$ alkyl,
  (c) C$_1$-C$_8$ perfluoroalkyl,
  (d) C$_3$-C$_6$ cycloalkyl,
  (e) phenyl,
  (f) benzyl;
R$^{16}$ is
  (a) H,
  (b) C$_1$-C$_6$ alkyl,
  (c) benzyl;
R$^{17}$ is
  (a) H,
  (b) C$_1$-C$_6$ alkyl,
  (c) C$_3$-C$_6$ cycloalkyl,
  (d) phenyl,
  (e) benzyl;
R$^{18}$ is
  (a) —NR$^{19}$R$^{20}$—,
  (b) —NHCONH$_2$,
  (c) —NHCSNH$_2$,
  (d) —NHSO$_2$-C$_6$H$_5$;
R$^{19}$ and R$^{20}$ are independently
  (a) H,
  (b) C$_1$-C$_5$ alkyl,
  (c) phenyl;
R$^{21}$ and R$^{22}$ are independently
  (a) C$_1$-C$_4$ alkyl or taken together are
  (b) —(CH$_2$)$_q$—;
L is a divalent group which is a
  (a) C$_1$ to C$_8$ alkylene chain,
  (b) C$_3$ to C$_8$ alkenylene chain,
  (c) C$_3$ to C$_8$ alkynylene chain,
  (d) C$_2$ to C$_8$ alkylene chain containing O,
  (e) C$_2$ to C$_8$ alkylene chain containing S(O)$_{0-2}$,
  (f) C$_2$ to C$_8$ alkylene chain containing NR$^{23}$;
  wherein the alkylene, alkenylene and alkynylene chains may be branched or unbranched, 0 to 1 carbon atoms of L may comprise a carbonyl group, and both termini of L comprise carbon atoms;
R$^{23}$ is
  (a) H,
  (b) C$_1$-C$_6$ alkyl,
  (c) C$_3$-C$_6$ alkenyl,
  (d) aryl,
  (e) aryl (C$_1$-C$_4$) alkyl,
  (f) C$_2$-C$_6$ alkanoyl,
  (g) arylcarbonyl
  (h) aryl (C$_1$-C$_4$) alkanoyl,
  (i) C$_1$-C$_6$ alkoxycarbonyl;
  where aryl and heteroaryl are as defined above;
A is a nitrogenous heterocyclic ring substituted by R$^{24}$ and R$^{25}$ and attached to L through nitrogen, consisting of a
  (a) piperidine,
  (b) 2-, 3-, or 4-piperidone,
  (c) 2,6-piperidinedione,
  (d) piperazine in which 0-2 ring carbons comprise carbonyl groups and N-4 is substituted by R$^{26}$ or R$^{28}$,
  (e) morpholine in which 0-2 ring carbons adjacent to nitrogen comprise carbonyl groups,
  (f) thiomorpholine in which 0-2 ring carbons adjacent to nitrogen comprise carbonyl groups and the sulfur may be mono- or dioxidized;
R$^{24}$ is
  (a) H,
  (b) C$_1$-C$_6$ alkyl,
  (c) aryl,
  (d) aryl (C$_1$-C$_4$) alkyl,
  (e) heteroaryl,
  (f) heteroaryl (C$_1$-C$_4$) alkyl,
  (g) diaryl (C$_1$-C$_4$) alkyl,
  (h) —OR$^{29}$,
  (i) —(CH$_2$)$_r$CO$_2$R$^{29}$,
  (j) —(CH$_2$)$_r$CH$_2$OR$^{29}$,
  (k) —(CH$_2$)$_r$CONR$^{31}$R$^{32}$,
  (l) —(CH$_2$)$_r$CH$_2$NR$^{31}$R$^{32}$,
  (m) —(CH$_2$)$_r$CH$_2$SH,
  (n) —(CH$_2$)$_r$CH$_2$S(O)$_{0-2}$R$^{30}$,
  (o) —(CH$_2$)$_r$CH$_2$NHC(NH$_2$)=NH;
  where aryl and heteroaryl are as defined above;
R$^{25}$ is
  (a) H,
  (b) C$_1$-C$_6$ alkyl,
  (c) aryl,
  (d) aryl (C$_1$-C$_4$) alkyl;
  where aryl is as defined above;
R$^{26}$ is
  (a) H,
  (b) C$_1$-C$_6$ alkyl,
  (c) C$_3$-C$_6$ cycloalkyl,
  (d) C$_4$-C$_8$ cycloalkylalkyl,
  (e) aryl,
  (f) heteroaryl,
  (g) aryl (C$_1$-C$_4$) alkyl,
  (h) heteroaryl (C$_1$-C$_4$) alkyl,
  (i) diaryl (C$_1$-C$_4$) alkyl,
  (j) (C$_3$-C$_6$ cycloalkyl) aryl (C$_1$-C$_4$) alkyl,
  (k) aryl (C$_3$-C$_6$) cycloalkyl,
  (l) C$_2$-C$_8$ alkoxyalkyl;
  where aryl and heteroaryl are as defined above;
R$^{28}$ is
  (a) C$_1$-C$_6$ alkanoyl,
  (b) arylcarbonyl,
  (c) aryl (C$_1$-C$_4$) alkanoyl,
  (d) diaryl (C$_1$-C$_4$) alkanoyl,
  (e) —CO$_2$R$^{33}$,
  (f) —CONR$^{31}$R$^{32}$,
  where aryl is as defined above;
R$^{29}$ is
  (a) H,
  (b) C$_1$-C$_6$ alkyl,
  (c) aryl,
  (d) aryl (C$_1$-C$_4$) alkyl,
  (e) diaryl (C$_1$-C$_4$) alkyl;
  where aryl is as defined above;
R$^{30}$ is
  (a) C$_1$-C$_6$ alkyl,
  (b) aryl,
  (c) aryl (C$_1$-C$_4$) alkyl,
  (d) diaryl (C$_1$-C$_4$) alkyl;
  where aryl is as defined above;
R$^{31}$ and R$^{32}$ are, independently (a) H,
(b) $C_1-C_6$ alkyl,
(c) aryl,
(d) aryl ($C_1-C_4$) alkyl;
where aryl is as defined above; or $R^{31}$ and $R^{32}$ when taken together constitute a pyrrolidine, piperidine or morpholine ring;

$R^{33}$ is
(a) $C_1-C_6$ alkyl,
(b) aryl,
(c) aryl ($C_1-C_4$) alkyl,
(d) diaryl ($C_1-C_4$) alkyl;
where aryl is as defined above;

$R^{34}$ is
(a) H,
(b) $C_1-C_4$ alkyl,
(c) $C_3-C_6$ cycloalkyl,
(d) aryl,
(e) aryl ($C_1-C_4$) alkyl;
where aryl is as defined above;

$R^{35}$ is
(a) H,
(b) $OR^{29}$,
(c) $NR^{38}R^{39}$;

$R^{36}$ and $R^{37}$ are independently
(a) H,
(b) $C_1-C_4$ alkyl,
(c) aryl,
(d) arylmethyl;

$R^{38}$ and $R^{39}$ are independently
(a) H,
(b) $C_1-C_4$ alkyl,
(c) aryl,
(d) arylmethyl,
or taken together comprise
(e) $-(CH_2)_u-$,
(f) a morpholine ring;
where aryl is as defined above;

X is
(a) a carbon-carbon single bond,
(b) $-CO-$,
(c) $-C(R^{19})(R^{20})-$,
(d) $-O-$,
(e) $-S-$,
(f) $-SO-$,
(g) $-SO_2-$,
(h) $-NR^{14}-$,
(i) $-CONR^{16}-$,
(j) $-NR^{16}CO-$,
(k) $-OC(R^{19})(R^{20})-$,
(l) $-C(R^{19})(R^{20})O-$,
(m) $-SC(R^{19})(R^{20})-$,
(n) $-C(R^{19})(R^{20})S-$,
(o) $-NHC(R^{19})(R^{20})-$,
(p) $-C(R^{19})(R^{20})NH-$,
(q) $-NR^{16}SO_2-$,
(r) $-SO_2NR^{16}-$,
(s) $-CH=CH-$,
(t) $-CF=CF-$,
(u) $-CH=CH-$,
(v) $-CH=CF-$,
(w) $-CF_2CF_2-$,
(x) $-CH(OR^{15})-$,
(y) $-CH(OCOR^{17})-$,
(z) $-C(=NR^{18})-$,
(aa) $-C(OR^{21})(OR^{22})-$,
(bb) 1,2-cyclopropyl,
(cc) 1,1-cyclopropyl;

$Z^1$ and $Z^2$ are independently
(a) $-O-$,
(b) $-S-$,
(c) $-NR^{11}-$;

m is 1 to 5;
n is 0 to 2;
q is 2 to 3;
r is 0 to 2;
s is 0 to 5;
t is 0 to 3;
u is 2 to 5;

and pharmaceutically acceptable salts of these compounds;

provided that when A is piperidine, piperazine or morpholine and $R^{24}$ and $R^{25}$ are both H then at least one of an applicable condition (a)-(c) is true;
(a) $R^{26}$ is not H, $C_1-C_4$ alkyl, phenyl or o-methoxyphenyl;
(b) $R^1$ is (h), (j), (k), (m) where $R^{10}$ is not $CH_3$ or $CF_3$, (n), (t) where $R^9$ is not H, (u), or (v);
(c) $R^{13}$ is (g), (i), (j), (l) where $R^{10}$ is not $CH_3$ or $CF_3$, (m), (s) where $R^9$ is not H, (t), or (u).

One embodiment of the present invention are the compounds of Formula (Ia):

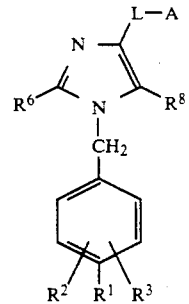

(Ia)

where $R^1$, $R^2$, $R^3$, $R^6$, $R^8$, L and A are as defined above. A preferred group of compounds within the compounds of Formula (Ia) are those wherein $R^1$ is
(a) $-CO_2H$,
(b) $-NHSO_2R^{10}$,
(c) $-SO_2NHCOR^{10}$,
(d) $-NHCONHSO_2R^{10}$,

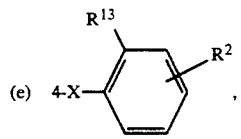

(e)

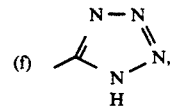

(f)

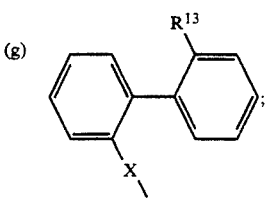

(g)

$R^6$ is
- (a) $C_1$-$C_{10}$ alkyl,
- (b) $C_3$-$C_{10}$ alkenyl,
- (c) $C_3$-$C_{10}$ alkynyl,
- (d) $C_3$-$C_8$ cycloalkyl,
- (e) benzyl, optionally substituted on the phenyl ring with one or two substitutents selected from the group consisting of halo, $C_1$-$C_4$ alkyl, $C_1$-$C_4$ alkoxy and —$NO_2$;

$R^{13}$ is
- (a) —$CO_2H$,
- (b) —$CONHSO_2R^{10}$,
- (c) —$NHCONHSO_2R^{10}$,
- (d) —$NHSO_2R^{10}$,
- (e) —$NHSO_2NHCOR^{10}$,
- (f) —$PO_3H_2$,
- (g) —$SO_3H$,
- (h) —$SO_2NHR^9$,
- (i) —$SO_2NHCOR^{10}$,
- (j) —$SO_2NHCONHR^9$, (k) 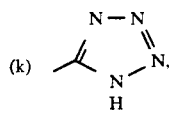

(l) 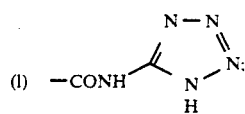

A is a heterocyclic ring substituted by $R^{24}$ and $R^{25}$ consisting of a
- (a) piperazine in which 0-2 ring carbons comprise carbonyl groups and N-4 is substituted by $R^{26}$ or $R^{28}$,
- (b) morpholine in which 0-2 ring carbons adjacent to nitrogen comprise a carbonyl groups,
- (c) thiomorpholine in which 0-2 ring carbons adjacent to nitrogen comprise a carbonyl groups and the sulfur may be mono- or dioxidized;

$R^{23}$ is
- (a) H,
- (b) $C_1$-$C_4$ alkyl,
- (c) allyl,
- (d) aryl,
- (e) arylmethyl,
- (f) $C_2$-$C_6$ alkanoyl,
- (g) arylcarbonyl,
- (h) arylacetyl,
- (i) $C_1$-$C_4$ alkoxycarbonyl; where aryl and heteroaryl are as defined above;

$R^{24}$ is
- (a) H,
- (b) $C_1$-$C_6$ alkyl,
- (c) aryl,
- (d) arylmethyl,
- (e) heteroaryl,
- (f) heteroarylmethyl,
- (g) diarylmethyl,
- (h) —$(CH_2)_rCO_2R^{29}$,
- (i) —$(CH_2)_rCH_2OR^{29}$,
- (j) —$(CH_2)_rCONR^{31}R^{32}$,
- (k) —$(CH_2)_rCH_2NR^{31}R^{32}$,
- (l) —$(CH_2)_rCH_2SH$,
- (m) —$(CH_2)_rCH_2S(O)_{0-2}R^{30}$,
- (n) —$(CH_2)_rCH_2NHC(NH_2)$=$NH$;

where aryl and heteroaryl are as defined above;

$R^{25}$ is
- (a) H,
- (b) $C_1$-$C_6$ alkyl,
- (c) aryl,
- (d) arylmethyl;
where aryl is as defined above;

$R^{26}$ is
- (a) H,
- (b) $C_1$-$C_6$ alkyl,
- (c) $C_3$-$C_6$ cycloalkyl,
- (d) $C_4$-$C_8$ cycloalkylalkyl,
- (e) aryl,
- (f) heteroaryl,
- (g) arylmethyl,
- (h) heteroarylmethyl,
- (i) diarylmethyl,
- (j) aryl($C_3$-$C_6$ cycloalkyl)methyl,
- (k) aryl ($C_3$-$C_6$) cycloalkyl,
- (l) $C_2$-$C_4$ alkoxyalkyl;
where aryl and heteroaryl are as defined above;

$R^{28}$ is
- (a) $C_1$-$C_6$ alkanoyl,
- (b) arylacetyl,
- (c) diarylacetyl,
- (d) —$CO_2R^{33}$,
- (e) —$CONR^{31}R^{32}$;
where aryl is as defined above;

$R^{29}$ is
- (a) H,
- (b) $C_1$-$C_4$ alkyl,
- (c) aryl,
- (d) arylmethyl,
- (e) diarylmethyl;
where aryl is as defined above;

$R^{30}$ is
- (a) $C_1$-$C_4$ alkyl,
- (b) aryl,
- (c) arylmethyl,
- (d) diarylmethyl;
where aryl is as defined above;

$R^{31}$ and $R^{32}$ are, independently
- (a) H,
- (b) $C_1$-$C_4$ alkyl,
- (c) aryl,
- (d) arylmethyl;
where aryl is as defined above; or $R^{31}$ and $R^{32}$ when taken together constitute a morpholine ring;

$R^{33}$ is
- (a) $C_1$-$C_4$ alkyl,
- (b) aryl,
- (c) arylmethyl,
where aryl is as defined above;

$R^{34}$ is
- (a) H,
- (b) $C_1$-$C_4$ alkyl,
- (c) aryl,
- (d) arylmethyl;
wherein aryl is as defined above;

$R^{35}$ is
- (a) H,
- (b) $OR^{29}$,
- (c) $NR^{38}R^{39}$;

$R^{38}$ and $R^{39}$ are independently
- (a) H,
- (b) $C_1$-$C_4$ alkyl
- (c) aryl,
- (d) arylmethyl, or taken together comprise (e) a piperidine ring,
(f) a morpholine ring;
where aryl is as defined above;
X is
(a) a carbon-carbon single bond,
(b) —CO—,
(c) —O—,
(d) —S—,
(e) —CONR$^{16}$—,
(f) —NR$^{16}$CO—,
(g) —OCH$_2$—,
(h) —CH$_2$O—,
(h) —SCH$_2$—,
(j) —CH$_2$S—,
(k) —NHCH$_2$—,
(l) —CH$_2$NH—,
(m) —CH=CH—,
n is 0;
t is 0 to 2;
and pharmaceutically acceptable salts.

More preferred are those preferred compounds of Formula (Ia) wherein
R$^1$ is
(a) —CO$_2$H,
(b) —NHSO$_2$R$^{10}$,
(c) —SO$_2$NHCOR$^{10}$,
(d) —NHCONHSO$_2$R$^{10}$, (e) 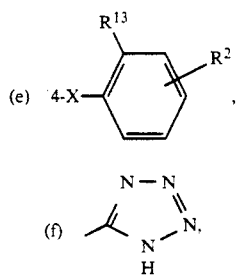

R$^2$ and R$^3$ are independently
(a) H,
(b) halo,
(c) C$_1$-C$_4$ alkyl,
(d) C$_1$-C$_4$ alkoxy;
R$^6$ is
(a) C$_2$-C$_7$ alkyl,
(b) C$_3$-C$_6$ alkenyl,
(c) C$_3$-C$_6$ alkynyl;
R$^{13}$ is
(a) —CO$_2$H,
(b) —CONHSO$_2$R$^{10}$,
(c) —NHCONHSO$_2$R$^{10}$,
(d) NHSO$_2$R$^{10}$,
(e) —NHSO$_2$NHCOR$^{10}$,
(f) —SO$_2$NHR$^9$,
(g) —SO$_2$NHCOR$^{10}$,
(h) SO$_2$NHCONHR$^9$, (i) 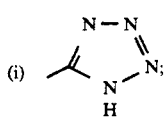

R$^{25}$ is H;
R$^{26}$ is
(a) H,
(b) C$_1$-C$_6$ alkyl,
(c) C$_3$-C$_6$ cycloalkyl,
(d) aryl,
(e) heteroaryl,
(f) arylmethyl,
(g) heteroarylmethyl,
where aryl and heteroaryl are as defined above;
R$^{30}$ is
(a) C$_1$-C$_4$ alkyl,
(b) aryl,
(c) arylmethyl,
where aryl is as defined above;
R$^{34}$ is H;
R$^{35}$ is
(a) H,
(b) OR$^{29}$,
(c) NR$^{38}$R$^{39}$;
R$^{36}$ and R$^{37}$ are H;
R$^{38}$ and R$^{39}$ are independently
(a) H,
(b) C$_1$-C$_4$ alkyl,
(c) aryl,
(d) arylmethyl,
or taken together comprise
(e) a piperidine ring,
(f) a morpholine ring;
where aryl is as defined above;
X is
(a) a carbon-carbon single bond,
(b) —O—,
(c) —CO—,
(d) —NHCO—,
(e) —OCH$_2$—; and pharmaceutically acceptable salts.

Most preferred are those more preferred compounds of Formula (Ia) wherein
R$^1$ is

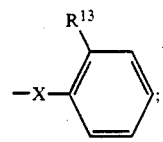

R$^{24}$ is
(a) H,
(b) C$_1$-C$_6$ alkyl,
(c) aryl,
(d) arylmethyl,
where aryl is as defined above;
R$^{26}$ is
(a) H,
(b) C$_1$-C$_6$ alkyl,
(c) aryl,
(d) arylmethyl,
where aryl is as defined above;
R$^{35}$ is
(a) H,
(b) —OR$^{29}$,
X is a carbon-carbon single bond;
and pharmaceutically acceptable salts.

A particular embodiment of the present invention is comprised of those most preferred compounds wherein A is a heterocyclic ring substituted by R$^{24}$ and R$^{25}$ consisting of a
(a) piperazine in which 1-2 ring carbons comprise a carbonyl group and N-4 is substituted by R$^{26}$ or R$^{28}$, (b) morpholine in which 1–2 ring carbons adjacent to nitrogen comprise a carbonyl group,
(c) thiomorpholine in which 0–2 ring carbons adjacent to nitrogen comprise a carbonyl group and the sulfur may be mono- or dioxidized; and R$^{13}$ is
(a) —CO$_2$H,
(b) —CONHSO$_2$R$^{10}$,
(d) —NHSO$_2$R$^{10}$,

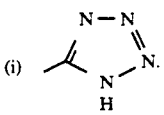

A further particular embodiment of the present invention is comprised of those most preferred compounds wherein A is a heterocyclic ring substituted by R$^{24}$ and R$^{25}$ consisting of a
(a) piperazine in which 1–2 ring carbons comprise a carbonyl group and N-4 is substituted by R$^{26}$ or R$^{28}$,
(b) morpholine in which 1–2 ring carbons adjacent to nitrogen comprise a carbonyl group,
(c) thiomorpholine in which 1–2 ring carbons adjacent to nitrogen comprise a carbonyl group and the sulfur may be mono- or dioxidized; and R$^{13}$ is
(c) —NHCONHSO$_2$R$^{10}$,
(e) —NHSO$_2$NHCOR$^{10}$,
(g) —SO$_2$NHCOR$^{10}$,
(h) —SO$_2$NHCONHR$^9$,
(f) —SO$_2$NHR$^9$.

A further particular embodiment of the present invention is comprised of those most preferred compounds wherein A is a heterocyclic ring substituted by R$^{24}$ and R$^{25}$ consisting of a
(a) piperazine where N-4 is substituted by R$^{26}$ or R$^{28}$,
(b) morpholine,
(c) thiomorpholine where the sulfur may be mono- or dioxidized; and R$^{13}$ is
(c) —NHCONHSO$_2$R$^{10}$
(e) —NHSO$_2$NHCOR$^{10}$,
(g) —SO$_2$NHCOR$^{10}$,
(h) —SO$_2$NHCONHR$^9$,
(f) —SO$_2$NHR$^9$.

Specific compounds illustrative of of this invention are the following:

5-Carboxy-4-(3,5-dimethylmorpholin-4-yl)methyl-2-propyl-1-[(2'-(tetrazol-5-yl)biphen-4-yl)methyl]-imidazole;

5-Carboxy-4-(thiomorpholin-4-yl)methyl-2-propyl-1-[(2'-(tetrazol-5-yl)biphen-4-yl)methyl]-imidazole;

5-Carboxy-4-(4-piperidon-1-yl)methyl-2-propyl-1-[(2'-(tetrazol-5-yl)biphen-4-yl)methyl]-imidazole;

5-Carboxy-4-(4-phenylpiperidin-1-yl)methyl-2-propyl-1-[(2'-(tetrazol-5-yl)biphen-4-yl)methyl]-imidazole;

5-Carboxy-4-(4-phenyl-2-piperidon-1-yl)methyl-2-propyl-1-[(2'-(tetrazol-5-yl)biphen-4-yl)methyl]-imidazole;

5-Carboxy-4-[4-(2-pyridyl)-piperazin-1-yl]methyl-2-ethyl-1-[(2'-(tetrazol-5-yl)biphen-4-yl)methyl]-imidazole;

5-Carboxy-4-[4-(2-pyridyl)-piperazin-1-yl]methyl-2-propyl-1-[(2'-(tetrazol-5-yl)biphen-4-yl)methyl]-imidazole;

5-Carboxy-4-[4-(2-pyridyl)-piperazin-1-yl]methyl-2-propyl-1-[(2-fluoro-2'-(tetrazol-5-yl)biphen-4-yl)methyl]-imidazole;

5-Methoxycarbonyl-4-[4-(2-pyridyl)-piperazin-1-yl]methyl-2-propyl-1-[(2'-(tetrazol-5-yl)biphen-4-yl)methyl]-imidazole;

5-Hydroxymethyl-4-[4-(2-pyridyl)-piperazin-1-yl]methyl-2-propyl-1-[(2'-(tetrazol-5-yl)biphen-4-yl)methyl]-imidazole;

4-[4-(2-Pyridyl)-piperazin-1-yl]methyl-2-propyl-1-[(2'-(tetrazol-5-yl)biphen-4-yl)methyl]-imidazole-5-carboxaldehyde;

5-Carboxy-4-[4-(2-pyridyl)-piperazin-1-yl]carbonyl-2-propyl-1-[(2'-(tetrazol-5-yl)biphen-4-yl)methyl]-imidazole;

5-Methoxycarbonyl-4-[4-(2-pyridyl)-piperazin-1-yl]carbonyl-2-propyl-1-[(2'-(tetrazol-5-yl)biphen-4-yl)methyl]-imidazole;

5-Carboxy-4-[4-(2-pyridyl)-piperazin-2-on-1-yl]methyl-2-propyl-1-[(2'-(tetrazol-5-yl)biphen-4-yl)methyl]-imidazole;

5-Carboxy-4-[4-(2-pyridyl)-piperazin-3-on-1-yl]methyl-2-propyl-1-[(2'-(tetrazol-5-yl)biphen-4-yl)methyl]-imidazole;

5-Carboxy-4-[4-(4-acetyl)phenylpiperazin-1-yl]methyl-2-propyl-1-[(2'-(tetrazol-5-yl)biphen-4-yl)methyl]-imidazole;

5-Methoxycarbonyl-4-[4-(4-acetyl)phenylpiperazin-1-yl]methyl-2-propyl-1-[(2'-(tetrazol-5-yl)biphen-4-yl)methyl]-imidazole;

5-Carboxy-4-[4-(2-chlorophenyl)-piperazin-1-yl]methyl-2-propyl-1-[(2'-(tetrazol-5-yl)biphen-4-yl)methyl]-imidazole;

5-Carboxy-4-[4-(3-methoxyphenyl)-piperazin-1-yl]methyl-2-propyl-1-[(2'-(tetrazol-5-yl)biphen-4-yl)methyl]-imidazole;

5-Carboxy-4-[4-(3-trifluoromethylphenyl)-piperazin-1-yl]methyl-2-propyl-1-[(2'-(tetrazol-5-yl)biphen-4-yl)methyl]-imidazole;

5-Methoxycarbonyl-4-[4-(3-trifluoromethylphenyl)-piperazin-1-yl]methyl-2-propyl-1-[(2'-(tetrazol-5-yl)biphen-4-yl)methyl]-imidazole;

5-Carboxy-4-(4-benzylpiperazin-1-yl)methyl-2-propyl-1-[(2'-(tetrazol-5-yl)biphen-4-yl)methyl]-imidazole;

5-Carboxy-4-[4-(2-trifluoromethylbenzyl)-piperazin-1-yl]methyl-2-propyl-1-[(2'-(tetrazol-5-yl)biphen-4-yl)methyl]-imidazole;

5-Carboxy-4-[4-(diphenylmethyl)-piperazin-1-yl]methyl-2-propyl-1-[(2'-(tetrazol-5-yl)biphen-4-yl)methyl]-imidazole;

5-Carboxy-4-{4-[phenyl(4-chlorophenyl)methyl]-piperazin-1-yl}methyl-2-propyl-1-[(2'-(tetrazol-5-yl)biphen-4-yl)methyl]-imidazole;

5-Carboxy-4-[4-(2-pyrimidinyl)-piperazin-1-yl]methyl-2-propyl-1-[(2'-(tetrazol-5-yl)biphen-4-yl)methyl]-imidazole;

5-Carboxy-4-(4-benzoylpiperazin-1-yl)methyl-2-propyl-1-[(240 -(tetrazol-5-yl)biphen-4-yl)methyl]-imidazole;

5-Carboxy-4-[4-(diphenylacetyl)piperazin-1-yl]methyl-2-propyl-1-[(2'-(tetrazol-5-yl)biphen-4-yl)methyl]-imidazole;

5-Carboxy-4-[4-(methoxycarbonyl)piperazin-1-yl]methyl-2-propyl-1-[(2'-tetrazol-5-yl)biphen-4-yl)methyl]-imidazole;

5-Carboxy-4-[4-(N,N-dibutylcarbamoyl)piperazin-1-yl]methyl-2-propyl-1-[(2'-(tetrazol-5-yl)biphen-4-yl)methyl]-imidazole;

1-[[2'-(N-Benzoyl)sulfonamidobiphen-4-yl]methyl]-5-carboxy-4-[4-(2-pyridyl)-piperazin-1-yl]methyl-2-propylimidazole.

Note that throughout the text when an alkyl substituent is mentioned, the normal alkyl structure is meant (e.g. butyl is n-butyl) unless otherwise specified. However, in the definition of radicals above (e.g. $R^6$), both branched and straight chains are included in the scope of alkyl, alkenyl and alkynyl.

Pharmaceutically acceptable salts include both the metallic (inorganic) salts and organic salts; a list of which is given in *Remington's Pharmaceutical Sciences* 17th Edition, pg. 1418 (1985). It is well known to one skilled in the art that an appropriate salt form is chosen based on physical and chemical stability, flowability, hydroscopicity and solubility. Preferred salts of this invention for the reasons cited above include potassium, sodium, calcium and ammonium salts.

Also within the scope of this invention are pharmaceutical compositions comprising a suitable pharmaceutical carrier and a novel compound of Formula (I), and methods of using the novel compounds of Formula (I) to treat hypertension and congestive heart failure. The pharmaceutical compositions can optionally contain one or more other therapeutic agents, such as a diuretic, an angiotensin-I converting enzyme (ACE) inhibitor or a non-steroidal antiinflammatory drug (NSAID). Also within the scope of this invention is a method of preventing renal failure resulting from administration of a NSAID which comprises administering a novel compound of Formula (I) in stepwise or physical combination with the NSAID. The compounds of this invention can also be used as diagnostic agents to test the renin angiotensin system.

It should be noted in the foregoing structural formula, when a radical can be a substituent in more than one previously defined radical, that first radical can be selected independently in each previously defined radical. For example, $R^1$, $R^2$ and $R^{13}$ can each be —CONHOR$^{12}$. $R^{12}$ need not be the same substituent in each of $R^1$, $R^2$ and $R^{13}$, but can be selected independently for each of them.

It is understood that many of the compounds of the present invention contain one or more chiral centers and that these stereoisomers may possess distinct physical and biological properties. The present invention comprises all of the stereoisomers or mixtures thereof. If the pure enantiomers or diastereomers are desired, they may be prepared using starting materials with the appropriate stereochemistry, or may be separated from mixtures of undesired stereoisomers by standard techniques, including chiral chromatography and recrystallization of diastereomeric salts.

Synthesis

The compounds of Formula (I) may be prepared using the reactions and techniques described in this section. The reactions are performed in solvent suitable to the reagents and materials employed and suitable for the transformation being effected. It is understood by those skilled in the art of organic synthesis that the functionality present on the imidazole and other portions of the molecule must be consistent with the chemical transformations proposed. This will frequently necessitate judgement as to the order of synthetic steps, protecting groups required, deprotection conditions and activation of a benzylic position to enable attachment to nitrogen on the imidazole nucleus. Throughout the following section, not all compounds of Formula (I) falling into a given class may necessarily be prepared by all the methods described for that class. Substituents on the starting materials may be incompatible with some of the reaction conditions required in some of the methods described. Such restrictions to the substituents which are compatible with the reaction conditions will be readily apparent to one skilled in the art and alternative methods described must then be used.

The compounds of Formula (I) where the heterocycle A is linked to L through a carbonyl group can be prepared by various methods depending on the heterocycle (Scheme (I)). Where a heterocycle is to be appended to L through a basic nitrogen, standard amide syntheses beginning with carboxylic acids (1) may be used (Thaler and Seebach, *Helv. Chim. Acta,* 74, 617, 1991). The acylation of aluminum and lithium salts of such heterocycles with imidazole ester (2), and the reaction of A-H with aldehyde (3) in the presence of appropriate oxidants also provides acyl-heterocycles of Formula (I). For lactam heterocycles, amide acylation procedures known to those skilled in the art may be employed (see Challis and Challis in Zabicky "The Chemistry of Amides" pp 731–857 Interscience, New York 1970; and Stack et al., *J. Am. Chem. Soc.,* 113, 5918, 1991). Where A is an imide, acylation may be accomplished using enol esters (Rothman, Serota and Swern, *J. Org. Chem.,* 29, 646, 1964) and acylsulfonates (Chiriac, *Rev. Roum. Chim.,* 32, 793, 1987).

Scheme I

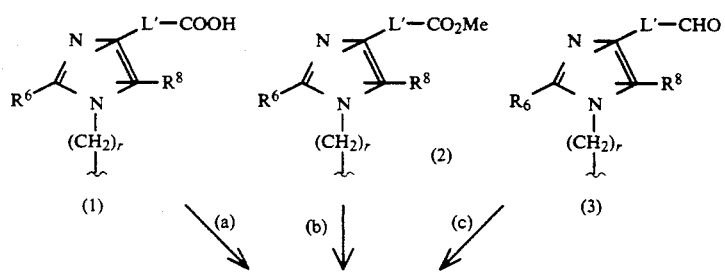

Scheme I -continued

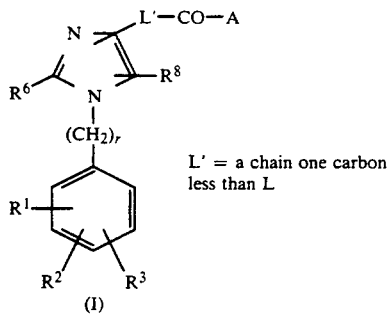

L' = a chain one carbon less than L (a) i. Activation with SOCl₂, carbonyldiimidazole or methanesulfonic anhydride;
ii. A-H, acid scavenger;
(b) A-M, where M is a metal such as Al or Li [J. I. Levin et al., Synthetic Communications, 12 (13), 989 (1982) and EP 324,377];
(c) NBS, AIBN A-H [I. E. Marko and A. Mekhalfia, Tetrahedron Lett., 31, No. 49, 7237 (1990)] or MnO₂, NaCN, A-H [W. Korytnyk et al., J. Med. Chem. 19, 999 (1976)].

The compounds of Formula (I) where A is linked to L through a methylene group may be obtained by reduction of acyl-heterocycles (I) (see Larock "Comprehensive Organic Transformations" p. 432 VCH, New York, 1989), by reductive amination of aldehyde (3) with A-H (see Abdel-Magid, Maryanoff and Carson, Tetrahedron Lett., 31, 5595, 1990 and references therein; also Katritzky et al. J. Org. Chem. 53, 5854, 1988 and J. Chem. Soc. Perkin Trans., I, 2339, 1988), or by the reaction of A-H or salts thereof with electrophiles (5) (examples of amine, amide and imide alkylations may be found in Larock [above cit.], pp. 397, 401, 909 and 990), the appropriate method being dependent on the heterocycle and other functionality present, as will be evident to one skilled in the art (Scheme II).

Scheme II

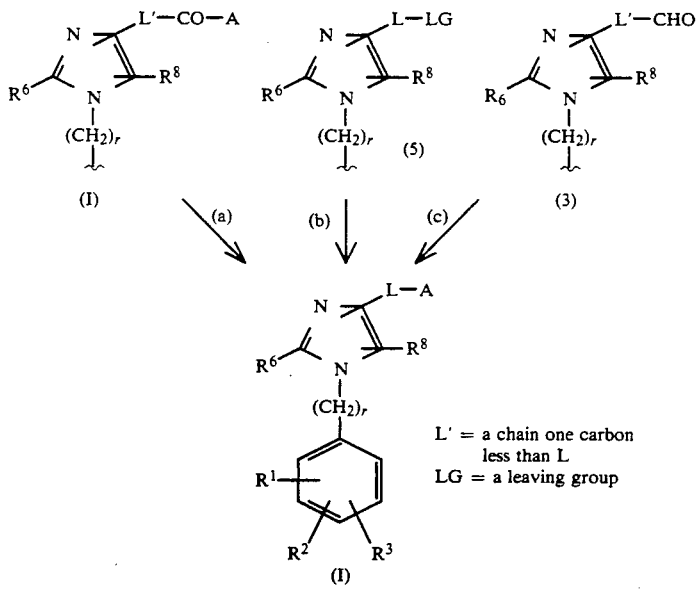

L' = a chain one carbon less than L
LG = a leaving group (a) LAH or BH₃; (b) A-metal or A—H, acid scavenger; (c) NaBH₃CN, A—H Intermediates such as carboxylic acids (1), esters (2), aldehydes (3), alcohols (4) and electrophiles (5) can be prepared from imidazole carboxylates as exemplified in Scheme III, and homologated, if desired, to precursors of Formula (I) compounds with various L linkers. For example, diester (2a) may be reduced with lithium aluminum hydride to diol (4b) (see EP 324377) or to ester-alcohol (4a) with DIBAL-H. Alcohols (4) may be oxidized with MnO2/CH₂Cl₂ to aldehydes (3) or converted to electrophiles such as mesylate (5a) using standard conditions.

Scheme III

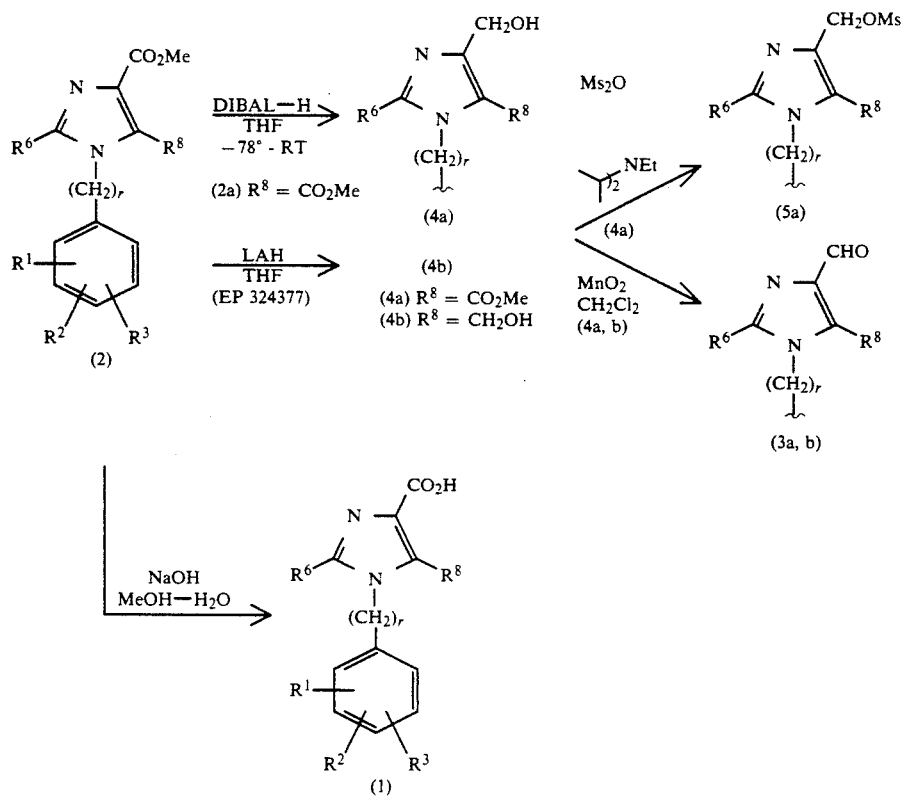

Typical homologation methods include Wittig reactions with aldehyde (3) (see US 90/03683) using phosphoranes containing alcohol (Maryanoff, Reitz and Duhl-Emswiler, [J. Am. Chem. Soc., 107, 217, 1985), nitrogen (Maryanoff et al., above cited, M. G. Nair, J. Org. Chem., 50, 1989, 1985, J. D. Coyle and P. A. Rapley, J. Chem. Research, (5), 142, 1986, W. Flitsch and K. Pasndl, Liebigs Ann. Chem., 649, 1987), aldehyde (see Rechka and Maxwell, Tetrahedron Lett., 29, 2599, 1988, Viala and Santelli, Synthesis, 395, 1988) and acid functionality (Maryanoff et al., above cited), optionally followed by reduction to the saturated intermediates. Wittig and related homologations using stabilized ylides or ylides with latent carbonyl functionality provide intermediates such as homologs of ester (2a) and aldehyde (3a) (see March "Advanced Organic Chemistry" pp. 845–854 Wiley, New York 1985; and Meyers, Tomoika and Fleming, J. Org. Chem., 43, 3788, 1978). Alternatively, the heterocycle may be incorporated into a suitable Wittig or Horner-Emmons reagent which is coupled with aldehyde (3) to give compounds of Formula (I).

Alcohol (4a) and homologs may be converted to the compounds of the present invention where L contains sulfide, sulfoxide or sulfone functionality by conversion to electrophiles (5) and reaction with difunctional thiols containing masked alcohol or aldehyde groups, optionally followed by oxidation at sulfur, deprotection and attachment of heterocycle A. Alternatively, reaction with thiol equivalents such as thiolacetic acid followed by conversion to free thiol and alkylation with suitably functionalized alkyl halides will also provide intermediates such as (2), (3) and (4) where L contains sulfur. Some of these intermediates have been described in copending U.S. application Ser. No. 07/545240, assigned to my assignee, and have activity as angiotensin-II receptor antagonists.

The synthesis of esters (2) from appropriate imidazoles (6) and aralkyl halides (7) has been described in U.S. 90/03683 and is exemplified in Scheme IV. The syntheses of the imidazoles and aralkyl halides have been described in U.S. Pat. No. 4,820,843, U.S. 90/03683, EP 324377, EP 400974 and EP 401030, which are hereby incorporated by reference. The imidazoles (6) may also be alkylated with, e.g., bromomethylaryl bromides (8) to give the (imidazolylmethyl)aryl Scheme IV

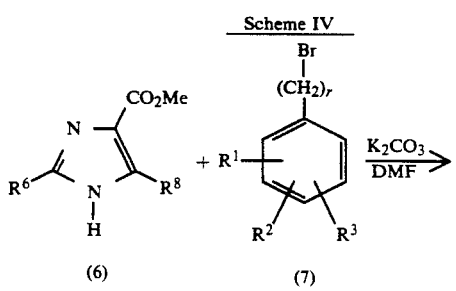

-continued
Scheme IV

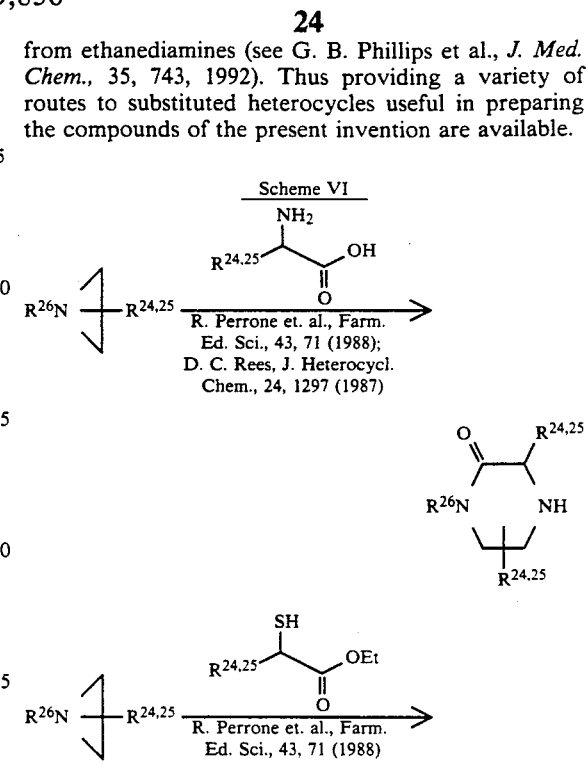

halides (9). These may be elaborated using the methods described above (Schemes I–III) to give heterocyclic imidazoles (10) and then coupled with appropriate aryl zinc reagents, stannanes or boronic acids (11) in the presence of palladium catalysts (see Larock "Comprehensive Organic Transformations" pp. 57, 58, 63–64 VCH, New York 1989) to give biphenylmethylimidazoles of Formula (1) (Scheme V). The aryl organometallics (11) may have $R^{13}$ substituents or groups which may be elaborated to $R^{13}$ using methods described in the references above.

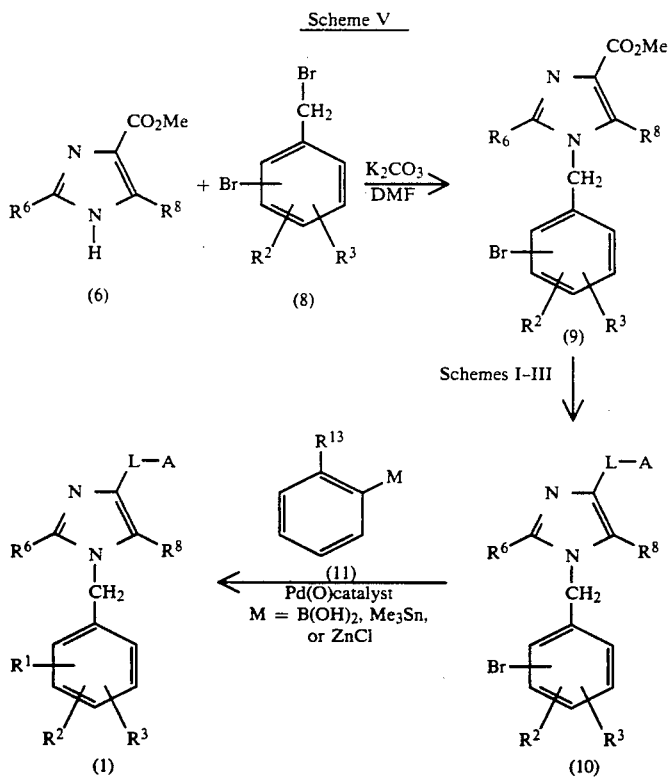

The heterocycles A–H used as intermediates in the procedures outlined above may be prepared by methods known in the art, examples of which are shown in Scheme V. The oxo-heterocycles shown in Scheme VI may be reduced to the corresponding di(tetra)hydro heterocycles with, e.g., $BH_3$ or lithium aluminum hydride (see S. D. Young et al., J. Org. Chem., 53, 1114, 1988 and J. H. Jones et al., J. Med. Chem., 27, 1607, 1984). Substituted piperazines are also available directly from ethanediamines (see G. B. Phillips et al., J. Med. Chem., 35, 743, 1992). Thus providing a variety of routes to substituted heterocycles useful in preparing the compounds of the present invention are available.

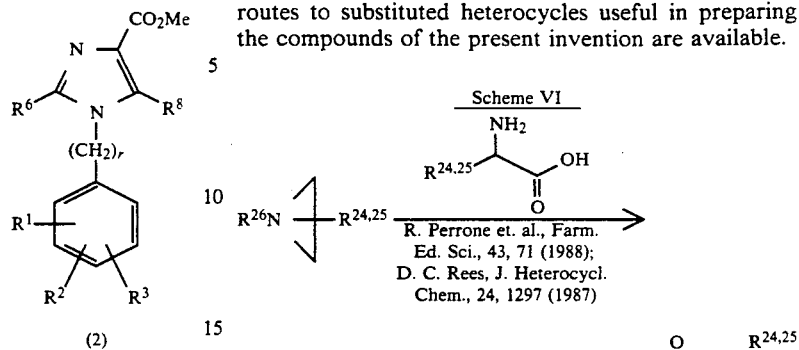

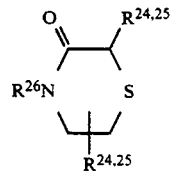

-continued
Scheme VI

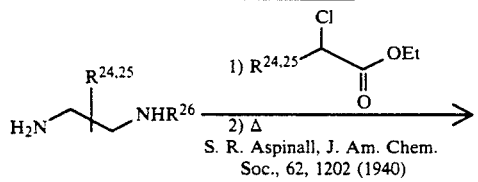

S. R. Aspinall, J. Am. Chem. Soc., 62, 1202 (1940)

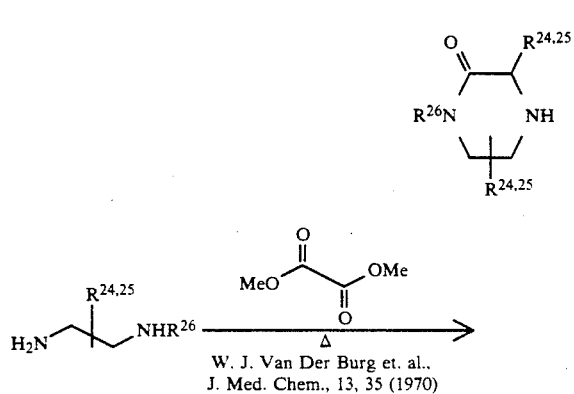

W. J. Van Der Burg et. al., J. Med. Chem., 13, 35 (1970)

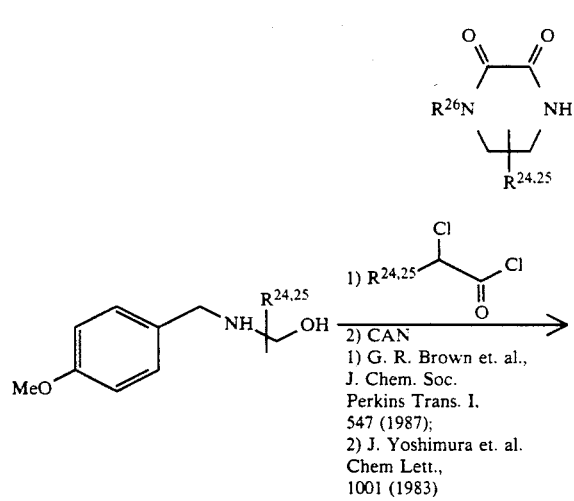

1) G. R. Brown et. al., J. Chem. Soc. Perkins Trans. I, 547 (1987);
2) J. Yoshimura et. al. Chem Lett., 1001 (1983)

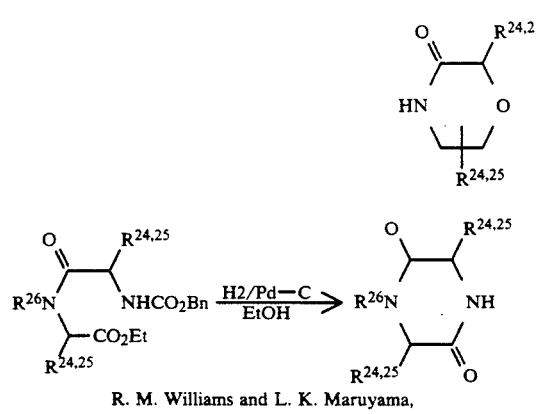

R. M. Williams and L. K. Maruyama, J. Org. Chem., 52, 4044 (1987)

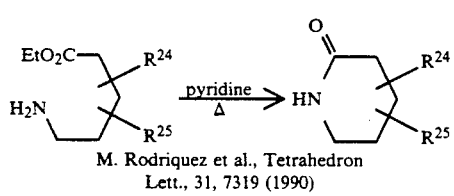

M. Rodriquez et al., Tetrahedron Lett., 31, 7319 (1990)

-continued
Scheme VI

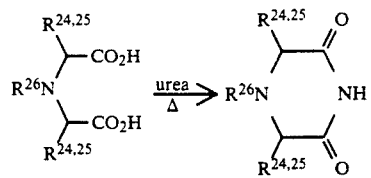

B. H. Chase and A. M. Downes, J. Chem. Soc., 3874 (1953)

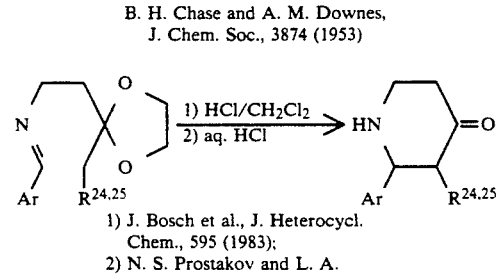

1) J. Bosch et al., J. Heterocycl. Chem., 595 (1983);
2) N. S. Prostakov and L. A. Gaivoronskaya, Russ. Chem. Rev., 47, 447 (1978)

Using the procedures shown in Scheme I and the references above, the following compounds of Formula (I) were prepared:

EXAMPLE 1

PART A: Preparation of 5-Methoxycarbonyl-4-[4-(2-pyridyl)-piperazin-1-yl]carbonyl-2-propyl-1-[(2'-(N-trityltetrazol-5-yl)biphen-4-yl)methyl]imidazole To a solution of 0.72 g (4.4 mmol) of 1-(2-pyridyl)piperazine in 10 mL of anhydrous $CH_2Cl_2$ under $N_2$ was added 4.4 mL (4.4 mmol) of a 1 N solution of HCl in ether. After 15 min., the suspension was cooled to 10° C. and treated with 2.2 mL (4.4 mmol) of 2.0 M $Me_3Al$ in toluene. Slow gas evolution was noted. After 30 min., a solution of 2.81 g (4.00 mmol) of 4,5-bis(methoxycarbonyl)-2-propyl-1-[(2'-(N-trityltetrazol-5-yl)biphen-4-yl)methyl]imidazole in 12 mL of $CH_2Cl_2$ was added. The reaction mixture was allowed to warm to room temperature and stir for 2 h, then partitioned between EtOAc and $H_2O$. The water layer was washed with EtOAc and the combined organic extracts were washed with water and brine, then dried over $MgSO_4$. After removal of solvents at reduced pressure, the residual tan foam (4.08 g) was purified using flash chromatography (eluent: 50/50 EtOAc-hexane to 1% MeOH-EtOAc) to give 2.36 g (71%) of the title compound as a white foam. $^1$H NMR (300 MHz, $CDCl_3$): δ0.88 (t, J=7.5 Hz, 3H, $CH_3$); 1.70 (sextet, J=7.5 Hz, 2H, $CH_2$); 2.52 (t, J=7.5 Hz, 2H, $CH_2$); 3.45 (m, 2H, piperazine); 3.54 (m, 2H, piperazine); 3.63 (m, 2H, piperazine); 3.71 (s, 3H, $CO_2CH_3$); 3.93 (m, 2H, piperazine); 5.46 (s, 2H, benzyl); 6.67 (m, 2H, aromatic); 6.82 (d, J=8.0 Hz, 2H, p-disubstituted aromatic); 6.94 (d, J=7.5 Hz, 6H, trityl); 7.11 (d, J=8.0 Hz, 2H, p-disubstituted aromatic); 7.2–7.4 (m, 10H, aromatic); 7.4–7.5 (m, 3H, aromatic); 7.91 (dd, J=7.0, 6.0 Hz, 1H, tetrazolyl-phenyl); 8.19 (approx. dd, J=5.5, 2.0 Hz, 1H, pyridyl).

PART B: Preparation of 5-Methoxycarbonyl-4-[4-(2-pyridyl)-piperazin-1-yl]carbonyl-2-propyl-1-[(2'-(tetrazol-5-yl)biphen-4-yl)methyl]imidazole A solution of 2.00 g (2.40 mmol) of the trityltetrazole obtained in Part A of Example 1 in 20 mL of MeOH was heated at reflux overnight. After cooling, 5 mL of 5% NaHCO₃ was added, and the solvents were removed under reduced pressure. The residue was partitioned between EtOAc and H₂O. The aqueous layer was extracted again with EtOAc, then partially evaporated under reduced pressure to remove residual EtOAc. Adjustment of the pH to 4.5 with aqueous HCl resulted in a white precipitate which was collected, washed with H₂O and suction dried under N₂ to give 1.21 g (85%) of the title compound. $^1$H NMR (300 MHz, CDCl₃): δ0.94 (t, J=7.5 Hz, 3H, CH₃); 1.73 (sextet, J=7.5 Hz, 2H, CH₂); 2.66 (t, J=7.5 Hz, 2H, CH₂); 3 39 (m, 2H, piperazine); 3.54 (m, 2H, piperazine); 3.62 (m, 2H, piperazine); 3.69 (s, 3H, CO₂CH₃); 3.89 (m, 2H, piperazine); 5.48 (s, 2H, benzyl); 6.69–6.74 (m, 2H); 6.87 (d, J=8.0 Hz, 2H, p-disubstituted aromatic); 7.04 (d, J=8.0 Hz, 2H, p-disubstituted aromatic); 7.40 (dd, J=7.5, 1.0 Hz, 1H); 7.46–7.59 (m, 3H); 7.81 (dd, J=7.5, 1.0 Hz, 1H, tetrazolyl-phenyl); 8.17 (dd, J=5.0, 1.0 Hz, 1H, pyridyl). IR (KBr) 2963, 1716, 1646, 1593, 1563, 1480, 1463, 1436, 1282, 1230, 1147 cm⁻¹. MS: m/z 592 (M+H).

EXAMPLE 2

Preparation of 5-Carboxy-4-[4-(2-pyridyl)-piperazin-1-yl]carbonyl-2-propyl-1-[(2'-(tetrazol-5-yl)biphen-4-yl)methyl-]imidazole The methyl ester obtained from Part B of Example 1 (0.592 g, 1.00 mmol) was stirred in 15 mL of 2:1 MeOH/3 N aqueous NaOH for 5 h. After removal of solvent under reduced pressure to near dryness, the residue was taken up in H₂O. This solution was filtered to remove particulates and adjusted to pH 5 with aqueous HCl. The resulting precipitate was collected, washed with H₂O and suction dried under N₂ to give 0.477 g (83%) of the title compound as an ivory powder. $^1$H NMR (300 MHz, CDCl₃): δ1.00 (t, J=7.5 Hz, 3H, CH₃); 1.80 (approx. sextet, J∼7.5 Hz, 2H, CH₂); 2.68 (t, J=7.5 Hz, 2H, CH₂); 3.73 (br m, 4H, piperazine); 3.97 (br s, 2H, piperazine); 4.61 (br s, 2H, piperazine); 5.71 (s, 2H, benzyl); 6.71 (approx. d, J∼9.0 Hz, 2H), 7.01 (d, J=8.0 Hz, 2H, p-disubstituted aromatic); 7.14 (d, J=8.0 Hz, 2H, p-disubstituted aromatic); 7.40 (approx. d, J=6.5 Hz, 1H); 7.50–7.59 (m, 3H); 8.05 (approx. d, J=8.0 Hz, 1H, tetrazolyl-phenyl); 8.19 (approx. d, J=3.5 Hz, 1H, pyridyl). IR (KBr) 3462 (br), 2964, 2930, 1710, 1640, 1594, 1551, 1480, 1437, 1232, 760 cm⁻¹. MS: m/z 578 (weak, M+H), 534 (strong, M+H —CO₂).

Using the procedures of Examples 1–2 and Scheme I, and the references above, the following Formula (I) compounds of Table 1 may be prepared:

TABLE 1

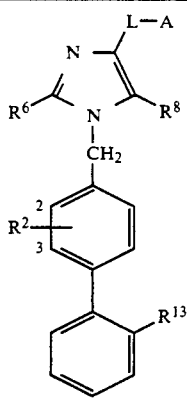

| Ex. No. | R² | R⁶ | R⁸ | L | A | R¹³ |
|---|---|---|---|---|---|---|
| 1 | H | n-C₃H₇ | CO₂CH₃ | CO | -N(piperazine)N-(2-pyridyl) | N=N, N—NH |
| 2 | H | n-C₃H₇ | CO₂H | CO | -N(piperazine)N-(2-pyridyl) | N=N, N—NH |
| 3 | H | n-C₃H₇ | CHO | CO | -N(piperazine)N-(2-pyridyl) | N=N, N—NH |
| 4 | H | n-C₃H₇ | CH₂OH | CO | -N(piperazine)N-(2-pyridyl) | N=N, N—NH |

TABLE 1-continued

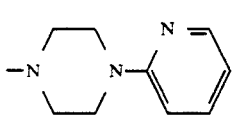

| Ex. No. | R² | R⁶ | R⁸ | L | A | R¹³ |
|---|---|---|---|---|---|---|
| 5 | H | n-C₃H₇ | ⟋⟍CO₂H (CH=CHCO₂H) | CO | -N(piperazine)N-(2-pyridyl) | N=N\N-C(CH₃)=NH (tetrazole-like) |
| 6 | H | n-C₃H₇ | CH₂OCH₃ | CO | -N(piperazine)N-(2-pyridyl) | N=N\N-C(CH₃)=NH |
| 7 | 2-F | n-C₃H₇ | CO₂H | CO | -N(piperazine)N-(2-pyridyl) | N=N\N-C(CH₃)=NH |
| 8 | 2-Cl | n-C₃H₇ | CO₂H | CO | -N(piperazine)N-(2-pyridyl) | N=N\N-C(CH₃)=NH |
| 9 | 2-Br | n-C₃H₇ | CO₂H | CO | -N(piperazine)N-(2-pyridyl) | N=N\N-C(CH₃)=NH |
| 10 | H | n-C₃H₇ | CO₂H | CH₂CO | -N(piperazine)N-(2-pyridyl) | N=N\N-C(CH₃)=NH |
| 11 | H | n-C₃H₇ | CO₂H | CH₂CH₂CO | -N(piperazine)N-(2-pyridyl) | N=N\N-C(CH₃)=NH |
| 12 | H | n-C₃H₇ | CO₂H | (CH₂)₃CO | -N(piperazine)N-(2-pyridyl) | N=N\N-C(CH₃)=NH |
| 13 | H | n-C₃H₇ | CO₂H | CH=CHCO | -N(piperazine)N-(2-pyridyl) | N=N\N-C(CH₃)=NH |

TABLE 1-continued

| Ex. No. | R² | R⁶ | R⁸ | L | A | R¹³ |
|---|---|---|---|---|---|---|
| 14 | H | n-C₃H₇ | CO₂H | −CH₂N(Ac)CHO | −N(piperazinyl)-pyridin-2-yl | tetrazolyl-like (N=N, N, NH, with CH₃) |
| 15 | H | n-C₃H₇ | CO₂H | −CH₂OCHO | −N(piperazinyl)-pyridin-2-yl | same |
| 16 | H | n-C₃H₇ | CO₂H | −CH₂SCHO | −N(piperazinyl)-pyridin-2-yl | same |
| 17 | H | n-C₃H₇ | CO₂H | −CH₂S(O)CHO | −N(piperazinyl)-pyridin-2-yl | same |
| 18 | H | n-C₃H₇ | CO₂H | −CH₂S(O)₂CHO | −N(piperazinyl)-pyridin-2-yl | same |
| 19 | H | n-C₃H₇ | CO₂H | CO | −N(piperazinyl)-pyridin-2-yl | −SO₂NHC(O)Ph |
| 20 | H | n-C₃H₇ | CO₂H | CO | −N(piperazinyl)-pyridin-2-yl | −SO₂NHC(O)-cyclopropyl |
| 21 | H | n-C₃H₇ | CO₂H | CO | −N(piperazinyl)-pyridin-2-yl | −SO₂NHC(O)-n-Pr |
| 22 | H | n-C₃H₇ | CO₂H | CO | −N(piperazinyl)-pyridin-2-yl | −NHC(O)N(NH)SO₂CH₃ |

TABLE 1-continued

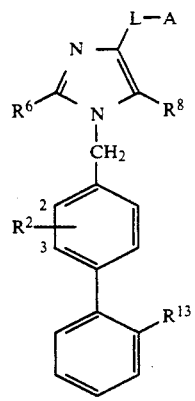

| Ex. No. | $R^2$ | $R^6$ | $R^8$ | L | A | $R^{13}$ |
|---|---|---|---|---|---|---|
| 23 | H | n-$C_3H_7$ | $CO_2H$ | CO | -N(piperazinyl)-2-pyridyl | -NHSO$_2$NHC(O)Ph |
| 24 | H | n-$C_3H_7$ | $CO_2H$ | CO | -N(piperazinyl)-2-pyridyl | -NHSO$_2$NHC(O)NHPh |
| 25 | H | n-$C_3H_7$ | $CO_2H$ | CO | -N(piperazinyl)-2-pyridyl | -NHSO$_2$-(1,3,5-triazin-2-yl) |
| 26 | H | n-$C_4H_9$ | $CO_2H$ | CO | -N(piperazinyl)-2-pyridyl | tetrazol-5-yl (NH) |
| 27 | H | $C_2H_5$ | $CO_2H$ | CO | -N(piperazinyl)-2-pyridyl | tetrazol-5-yl (NH) |
| 28 | H | $C_2H_5$CH=CH- | $CO_2H$ | CO | -N(piperazinyl)-2-pyridyl | tetrazol-5-yl (NH) |
| 29 | H | n-$C_3H_7$ | $CO_2H$ | CO | -N(3-methylpiperazinyl)phenyl | tetrazol-5-yl (NH) |
| 30 | H | n-$C_3H_7$ | $CO_2H$ | CO | -N(3-n-pentylpiperazinyl)phenyl | tetrazol-5-yl (NH) |

TABLE 1-continued

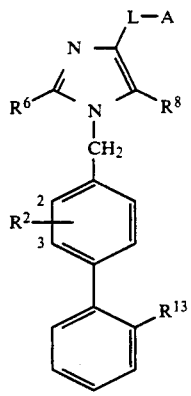

| Ex. No. | $R^2$ | $R^6$ | $R^8$ | L | A | $R^{13}$ |
|---|---|---|---|---|---|---|
| 31 | H | n-$C_3H_7$ | $CO_2H$ | CO | -N(piperazinyl, 2-$CH_2Ph$)-N-phenyl | N=N, N–C(CH$_3$)=NH |
| 32 | H | n-$C_3H_7$ | $CO_2H$ | CO | -N(piperazinyl, 2-$CH_2Ph$)-N-(2-pyridyl) | N=N, N–C(CH$_3$)=NH |
| 33 | H | n-$C_3H_7$ | $CO_2H$ | CO | -N(piperazinyl, 2-Ph)-N-phenyl | N=N, N–C(CH$_3$)=NH |
| 34 | H | n-$C_3H_7$ | $CO_2H$ | CO | -N(piperazinyl, 2-$CH_3$)-N-phenyl | N=N, N–C(CH$_3$)=NH |
| 35 | H | n-$C_3H_7$ | $CO_2H$ | CO | -N(piperazinyl, 2-n-$C_5H_{11}$)-N-phenyl | N=N, N–C(CH$_3$)=NH |
| 36 | H | n-$C_3H_7$ | $CO_2H$ | CO | -N(piperazinyl, 3-$CH_2Ph$)-N-phenyl | N=N, N–C(CH$_3$)=NH |
| 37 | H | n-$C_3H_7$ | $CO_2H$ | CO | -N(piperazinyl, 3-Ph)-N-phenyl | N=N, N–C(CH$_3$)=NH |

TABLE 1-continued

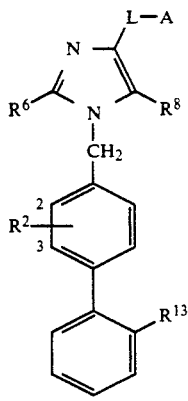

| Ex. No. | R² | R⁶ | R⁸ | L | A | R¹³ |
|---|---|---|---|---|---|---|
| 38 | H | n-C₃H₇ | CO₂H | CO | piperazine with NCH₂Ph, CH₃ substituent | N=N, N⧸⧹NH (C-CH₃) |
| 39 | H | n-C₃H₇ | CO₂H | CO | piperazine with NCH₂Ph, Ph substituent | N=N, N⧸⧹NH |
| 40 | H | n-C₃H₇ | CO₂H | CO | piperazine with NCH₂Ph, CH₃ substituent | N=N, N⧸⧹NH |
| 41 | H | n-C₃H₇ | CO₂H | CO | piperazine with NCH₂Ph, Ph substituent | N=N, N⧸⧹NH |
| 42 | H | n-C₃H₇ | CO₂H | CO | piperazine-N(p-F—Ph) | N=N, N⧸⧹NH |
| 43 | H | n-C₃H₇ | CO₂H | CO | piperazine-N(p-Me—Ph) | N=N, N⧸⧹NH |
| 44 | H | n-C₃H₇ | CO₂H | CO | piperazine-(2-pyrimidinyl) | N=N, N⧸⧹NH |
| 45 | H | n-C₃H₇ | CO₂H | CO | piperazine-(1,3,5-triazin-2-yl) | N=N, N⧸⧹NH |

TABLE 1-continued
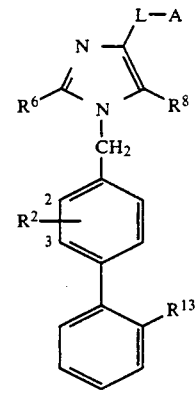
| Ex. No. | R² | R⁶ | R⁸ | L | A | R¹³ |
|---|---|---|---|---|---|---|
| 46 | H | n-C₃H₇ | CO₂H | CO | 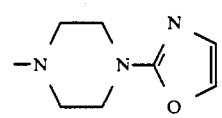 | 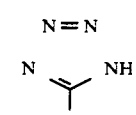 |
| 47 | H | n-C₃H₇ | CO₂H | CO | 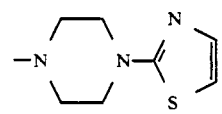 | 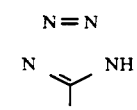 |
| 48 | H | n-C₃H₇ | CO₂H | CO | 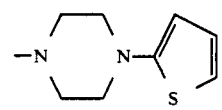 | 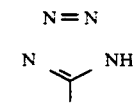 |
| 49 | H | n-C₃H₇ | CO₂H | CO | 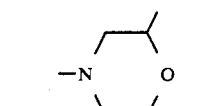 | 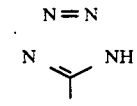 |
| 50 | H | n-C₃H₇ | CO₂H | CO | 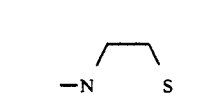 | 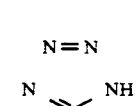 |
| 51 | H | n-C₃H₇ | CO₂H | CO | 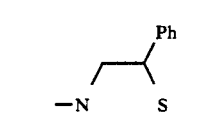 | 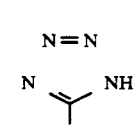 |
| 52 | H | n-C₃H₇ | CO₂H | CO | 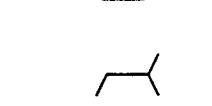 | 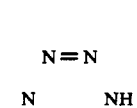 |
| 53 | H | n-C₃H₇ | CO₂H | CO | 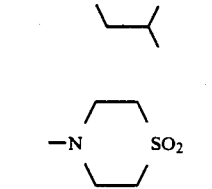 | 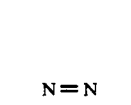 |

TABLE 1-continued

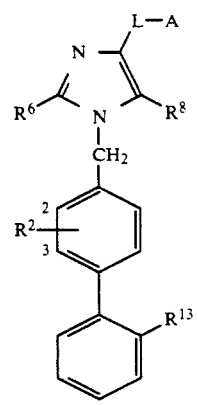

| Ex. No. | R² | R⁶ | R⁸ | L | A | R¹³ |
|---|---|---|---|---|---|---|
| 54 | H | n-C₃H₇ | CO₂H | CO | −N(CH₂CH₂)₂SO₂ with Ph substituent | N=N, N-NH, =C(CH₃) |
| 55 | H | n-C₃H₇ | CO₂H | CO | piperazinyl-C(O)-N(Bu)₂ | N=N, N-NH, =C(CH₃) |
| 56 | H | n-C₃H₇ | CO₂H | CO | piperazinyl-(2-pyridyl) | CO₂H |
| 57 | H | n-C₃H₇ | CO₂H | CO | piperazinone-N-phenyl | N=N, N-NH, =C(CH₃) |
| 58 | H | n-C₃H₇ | CO₂H | CO | piperazinone-N-phenyl (isomer) | N=N, N-NH, =C(CH₃) |
| 59 | H | n-C₃H₇ | CO₂H | CO | 2,6-dioxopiperazinyl-N-phenyl | N=N, N-NH, =C(CH₃) |
| 60 | H | n-C₃H₇ | CO₂CH₃ | CO | 2,3-dioxopiperazinyl-N-phenyl | N=N, N-NH, =C(CH₃) |
| 61 | H | n-C₃H₇ | CO₂H | CO | 2,6-dioxopiperazinyl-N-phenyl | N=N, N-NH, =C(CH₃) |

TABLE 1-continued

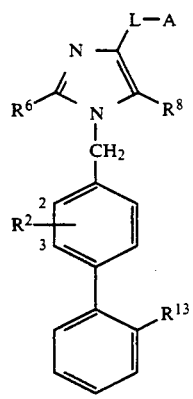

| Ex. No. | R² | R⁶ | R⁸ | L | A | R¹³ |
|---|---|---|---|---|---|---|
| 62 | H | n-C₃H₇ | CHO | CO | piperazine-2,5-dione, N'-phenyl | N=N, N-C(NH)- (aminotriazole) |
| 63 | H | n-C₃H₇ | CH₂OH | CO | 3-oxopiperazine, N'-CH₂Ph | N=N, N-C(NH)- |
| 64 | H | n-C₃H₇ | CO₂H | CO | 3-oxopiperazine, N'-CH₂Ph | N=N, N-C(NH)- |
| 65 | H | n-C₃H₇ | CO₂H | CO | 3-oxopiperazine, N'-n-Bu | N=N, N-C(NH)- |
| 66 | H | n-C₃H₇ | CO₂H | CO | 3-oxopiperazine, N'-n-Bu | N=N, N-C(NH)- |
| 67 | H | n-C₃H₇ | CO₂H | CO | 3-methyl-2-oxopiperazine, N'-phenyl | N=N, N-C(NH)- |
| 68 | H | n-C₃H₇ | CO₂H | CO | 3-methyl-2-oxopiperazine, N'-CH₂Ph | N=N, N-C(NH)- |

TABLE 1-continued

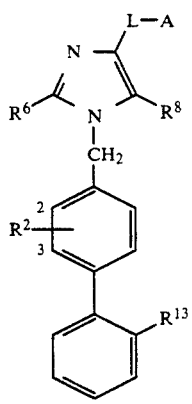

| Ex. No. | $R^2$ | $R^6$ | $R^8$ | L | A | $R^{13}$ |
|---|---|---|---|---|---|---|
| 69 | H | n-$C_3H_7$ | $CO_2H$ | CO | −N(CH$_3$)piperazine-N-n-Bu, ketone | N=N / N−NH tetrazole |
| 70 | H | n-$C_3H_7$ | $CO_2H$ | CO | −N(n-$C_5H_{11}$)piperazine-N-Ph, ketone | N=N / N−NH tetrazole |
| 71 | H | n-$C_3H_7$ | $CO_2H$ | CO | −N(n-$C_5H_{11}$)piperazine-NCH$_2$Ph, ketone | N=N / N−NH tetrazole |
| 72 | H | n-$C_3H_7$ | $CO_2H$ | CO | −N(n-$C_5H_{11}$)piperazine-N-n-Bu, ketone | N=N / N−NH tetrazole |
| 73 | H | n-$C_3H_7$ | $CO_2H$ | CO | −N(PhCH$_2$)piperazine-N-Ph, ketone | N=N / N−NH tetrazole |
| 74 | H | n-$C_3H_7$ | $CO_2H$ | CO | −N(PhCH$_2$)piperazine-NCH$_2$Ph, ketone | N=N / N−NH tetrazole |
| 75 | H | n-$C_3H_7$ | $CO_2H$ | CO | −N(PhCH$_2$)piperazine-N-n-Bu, ketone | N=N / N−NH tetrazole |

TABLE 1-continued

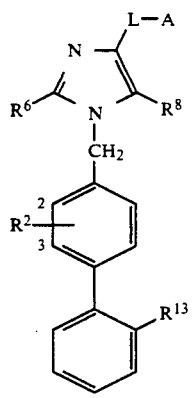

| Ex. No. | R² | R⁶ | R⁸ | L | A | R¹³ |
|---|---|---|---|---|---|---|
| 76 | H | n-C₃H₇ | CO₂H | CO | -N(piperazine with PhCH₂ and C=O)-N-pyridin-2-yl | N=N, N-C(CH₃)=NH |
| 77 | H | n-C₃H₇ | CO₂H | CO | -N(piperazine with Ph and C=O)-N-phenyl | N=N, N-C(CH₃)=NH |
| 78 | H | n-C₃H₇ | CO₂H | CO | -N(piperazine with Ph and C=O)-NCH₂Ph | N=N, N-C(CH₃)=NH |
| 79 | H | n-C₃H₇ | CO₂H | CO | -N(piperazine with Ph and C=O)-N-n-Bu | N=N, N-C(CH₃)=NH |
| 80 | H | n-C₃H₇ | CO₂H | CO | -N(piperazine with CH₃ and C=O)-N-phenyl | N=N, N-C(CH₃)=NH |
| 81 | H | n-C₃H₇ | CO₂H | CO | -N(piperazine with CH₃ and C=O)-NCH₂Ph | N=N, N-C(CH₃)=NH |
| 82 | H | n-C₃H₇ | CO₂H | CO | -N(piperazine with CH₃ and C=O)-N-n-Bu | N=N, N-C(CH₃)=NH |

TABLE 1-continued

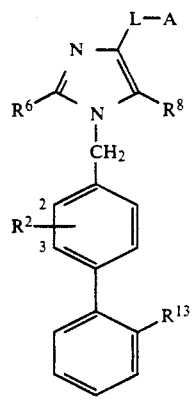

| Ex. No. | R² | R⁶ | R⁸ | L | A | R¹³ |
|---|---|---|---|---|---|---|
| 83 | H | n-C₃H₇ | CO₂H | CO | −N(piperazinone with N-Ph, n-C₅H₁₁) | N=N, N-NH (tetrazole-like amidine) |
| 84 | H | n-C₃H₇ | CO₂H | CO | −N(piperazinone with NCH₂Ph, n-C₅H₁₁) | N=N, N-NH |
| 85 | H | n-C₃H₇ | CO₂H | CO | −N(piperazinone with N-n-Bu, n-C₅H₁₁) | N=N, N-NH |
| 86 | H | n-C₃H₇ | CO₂H | CO | −N(piperazinone with N-Ph, CH₂Ph) | N=N, N-NH |
| 87 | H | n-C₃H₇ | CO₂H | CO | −N(piperazinone with NCH₂Ph, CH₂Ph) | N=N, N-NH |
| 88 | H | n-C₃H₇ | CO₂H | CO | −N(piperazinone with N-n-Bu, CH₂Ph) | N=N, N-NH |
| 89 | H | n-C₃H₇ | CO₂H | CO | −N(piperazinone with N-Ph, Ph) | N=N, N-NH |

TABLE 1-continued

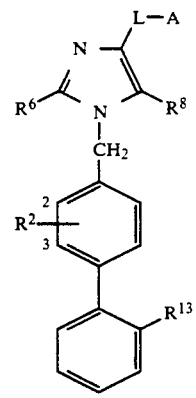

| Ex. No. | R² | R⁶ | R⁸ | L | A | R¹³ |
|---|---|---|---|---|---|---|
| 90 | H | n-C₃H₇ | CO₂H | CO | 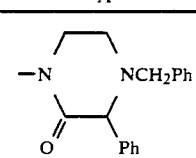 | $\begin{array}{c}N=N\\N\phantom{xx}NH\end{array}$ |
| 91 | H | n-C₃H₇ | CO₂H | CO | 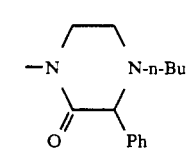 | $\begin{array}{c}N=N\\N\phantom{xx}NH\end{array}$ |
| 92 | H | n-C₃H₇ | CO₂H | CO | 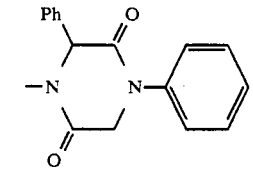 | $\begin{array}{c}N=N\\N\phantom{xx}NH\end{array}$ |
| 93 | H | n-C₃H₇ | CO₂H | CO | 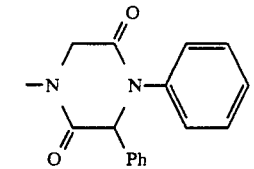 | $\begin{array}{c}N=N\\N\phantom{xx}NH\end{array}$ |
| 94 | H | n-C₃H₇ | CO₂H | CO | 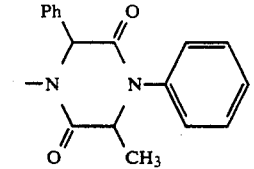 | $\begin{array}{c}N=N\\N\phantom{xx}NH\end{array}$ |
| 95 | H | n-C₃H₇ | CO₂H | CO | 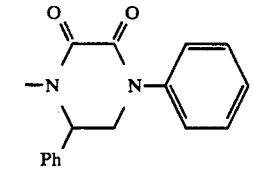 | $\begin{array}{c}N=N\\N\phantom{xx}NH\end{array}$ |
| 96 | H | n-C₃H₇ | CO₂H | CO | 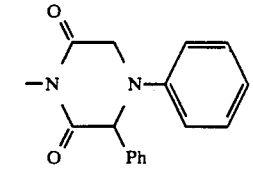 | $\begin{array}{c}N=N\\N\phantom{xx}NH\end{array}$ |

TABLE 1-continued

[Structure: imidazole with L-A at 4-position, R⁶ at 2-position, R⁸ at 5-position, N-CH₂ linked to biphenyl with R² on first ring and R¹³ on second ring ortho position]

| Ex. No. | R² | R⁶ | R⁸ | L | A | R¹³ |
|---|---|---|---|---|---|---|
| 97 | H | n-C₃H₇ | CO₂H | CO | piperazine-2,5-dione with N-phenyl and Ph substituent (−N linked, phenyl on N, Ph on ring carbon) | tetrazole (N=N, N, NH) |
| 98 | H | n-C₃H₇ | CO₂H | CO | morpholine-type: −N−CH(CH₃)−C(=O)− with O and CH(CH₃) | tetrazole |
| 99 | H | n-C₃H₇ | CO₂H | CO | thiomorpholine with Ph substituent: −N−CH(Ph)−C(=O)− with S | tetrazole |
| 100 | H | n-C₃H₇ | CO₂H | CO | thiomorpholine with CH₃ groups: −N−CH(CH₃)−C(=O)− with S and CH(CH₃) | tetrazole |

EXAMPLE 101

PART A: Preparation of 5-Methoxycarbonyl-4-hydroxymethyl-2-propyl-1-[(2'-(N-trityltetrazol-5-yl)biphen-4-yl)methyl]imidazole To a solution of 7.03 g (10.0 mmole) of 4,5-bis(methoxycarbonyl)-2-propyl-1-[(2'-(N-trityltetrazol-5-yl)biphen-4-yl)methyl]-imidazole in 80 mL anhydrous THF was added 20.0 mL 1.0M DIBAL-H (20.0 mmole, in THF) at −75° C. The mixture was stirred at −75° C. for 2.5 hours and then warmed to room temperature. After stirring overnight at room temperature, TLC (ethyl acetate) showed no starting material. The mixture was poured into 100 mL saturated aqueous NH₄Cl solution and stirred for 20 min.; the product was extracted with 4×200 mL ethyl acetate, and the combined organic layer was washed with brine, dried over MgSO₄, and filtered. Solvents were then removed under reduced pressure to yield 6.30 g (89.4%) of the title compound as a white foam. ¹H NMR (300 MHz, DMSO-d₆): δ0.77 (t, J=7.3 Hz, 3H); 1.55 (m, 2H); 2.44 (t, J=7.7 Hz, 3H); 3.66 (s, 3H); 4.59 (d, J=6.2 Hz, 2H); 4.82 (t, J=6.2 Hz, 1H); 5.49 (s, 2H); 6.80–7.80 (m, 23H). MS (NH₃—CI/DDIP): m/z 675 (M+H, 26%); 619 (M+H-N₄, 100%); 243 (Tr, 19%). Calculated mass for C₄₂H₃₉N₆O₃ (M+H): 675.308365; found: 675.308581.

PART B: Preparation of 5-Methoxycarbonyl-4-[4-(2-pyridyl)-piperazin-1-yl]methyl-2-propyl-1-[(2'-(N-trityltetrazol-5-yl)biphen-4-yl)methyl]imidazole To a solution of 0.97 g (5.56 mmol) methanesulfonic anhydride in 30 mL dichloromethane cooled at −50° C. was added a mixture of 3.00 g (4.45 mmol) of the hydroxymethylimidazole obtained from Part A of Example 101 and 1.94 mL (11 1 mmol) N,N-diisopropylethylamine in 20 mL dichloromethane. The reaction mixture was stirred at −42° C. for 2 hours and then warmed to −3° C. and stirred for another 2 hours after which no starting material was detected by TLC (ethyl acetate). 1-(2-Pyridyl)piperazine (0.85 mL, 5.56 mmol) was added to the reaction mixture at 0° C.; then the reaction was warmed to room temperature and stirred overnight. The reaction was worked-up by adding 100 mL water, extracting product with 4×150 mL ethyl acetate, washing combined organic layer with 5×200 mL water and 100 mL brine solution, drying over magnesium sulfate, filtering, and evaporating solvents under reduced pressure. The crude product was purified by flash chromatography (0-5% methanol in ethyl acetate) to yield 2.75 g (75%) of the title compound as a white foam. $^1$H NMR (300 MHz, CDCl$_3$): δ0.87 (t, J=7.3 Hz, 3H); 1.63 (m, 2H); 2.54 (t, J=7.7 Hz, 2H); 2.72 (br s, 4H, piperazine); 3.58 (br s, 4H, piperazine); 3.70 (s, 3H); 3.89 (s, 2H); 5.43 (s 2H); 6.58-8.19 (m, 27H). MS (NH$_3$—CI/DDIP): m/z 820 (M+H); 764 (M+H—N$_4$); 522 (M+H—N$_4$—Tr); 243 (Tr).

PART C: Preparation of 5-Methoxycarbonyl-4-[4-(2-pyridyl)-piperazin-1-yl]methyl-2-propyl-1-[(2'-(tetrazol-5-yl)biphen-4-yl)methyl]imidazole 5-Methoxycarbonyl-4-[4-(2-pyridyl)-piperazin-1-yl]methyl-2-propyl-1-[(2'-(N-trityltetrazol-5-yl)biphen-4-yl)methyl]imidazole (1.72 g, 2.10 mmol), obtained from Part B of Example 101, was stirred in 75 mL methanol at reflux for 2 hours. After evaporation of solvent under reduced pressure, the residue was stirred in 30 mL of 1:1 methanol/5% aqueous NaHCO$_3$ for 6 h. The reaction mixture was extracted with 4×50 mL ethyl ether, and the residual organic solvent in the aqueous layer was evaporated under reduced pressure. The product was precipitated by adjusting the pH to 5 with aqueous HCl. The title compound (1.02 g, 84.2%) was collected as a white powder after filtering and drying in vacuo at 60° C. $^1$H NMR (300 MHz, CDCl$_3$): δ0.86 (t, J=7.3 Hz, 3H); 1.61 (m, 2H); 2.54 (t, J=7.7 Hz, 2H); 2.76 (br s, 4H, piperazine); 3.54 (br s, 4H, piperazine); 3.63 (s, 3H); 3.88 (s, 2H); 5.27 (s, 2H); 6.57-8.13 (m, 12H).

EXAMPLE 102

Preparation of 5-Carboxy-4-[4-(2-pyridyl)-piperazin-1-yl]methyl-2-propyl-1-[(2'-(tetrazol-5-yl)biphen-4-yl)methyl]imidazole The methyl ester obtained from Part C of Example 101 was stirred in 40 mL of 1:1 methanol/3 N aqueous NaOH for 3.5 hours. The workup procedure described in Part C of Example 101 was followed to isolate the title compound. $^1$H NMR (300 MHz, DMSO-d$_6$): δ0.83 (t, J=7.3 Hz, 3H); 1.54 (m, 2H); 2.48 (t); 2.97 (br s, 4H, piperazine); 3.62 (br s, 4H, piperazine); 4.08 (s, 2H); 4.08 (s, 2H); 5.69 (s, 2H); 6.71-8.15 (m, 12H). MS (NH$_3$—DCI): m/z 581 (M+NH$_4$); 564 (M+H); 520 (M+H—CO$_2$). Calculated mass for C$_{31}$H$_{34}$N$_9$O$_2$ (M+H): 564.283547; found: 564.282518.

EXAMPLE 103

PART A: Preparation of 5-Methoxycarbonyl-4-[4-(4-acetyl)phenylpiperazin-1-yl]methyl-2-propyl-1-[(2'-(N-trityltetrazol-5-yl)biphen-4-yl)methyl]imidazole The title compound was synthesized using the hydroxymethylimidazole obtained from Part A of Example 101 and 4'-piperazinoacetophenone by the method described in Part B of Example 101. $^1$H NMR (300 MHz, CDCl$_3$): δ0.87 (t, J=7.3 Hz, 3H); 1.67 (m, 2H); 2.51 (s, 3H); 2.55 (t, J=7.7 Hz, 2H); 2.74 (br t, 4H); 3.39 (br t, 4H); 3.71 (s, 3H); 3.89 (s, 2H); 5.43 (s, 2H); 6.74-7.92 (m, 27H). MS (NH$_3$—DCI): m/z 861 (M+H); 805 (M+H—N$_4$); 243 (Tr).

PART B: Preparation of 5-Methoxycarbonyl-4-[4-(4-acetyl)phenylpiperazin-1-yl]methyl-2-propyl-1-[(2'-(tetrazol-5-yl)biphen-4-yl)methyl]imidazole The title compound was synthesized using the corresponding trityltetrazole analog obtained from Part A of Example 103 by the procedures outlined in Part C of Example 101. $^1$H NMR (300 MHz, DMSO-d$_6$): δ0.86 (t, J=7.3 Hz, 3H); 1.60 (m, 2H); 2.44 (s, 3H); 2.59 (t, J=7.7 Hz, 2H ; 2.68 (br t, 4H); 3.35 (br t, 4H); 3.74 (s, 3H); 3.83 (s, 2H); 5.53 (s, 2H); 6.87-7.81 (m, 12H). MS NH$_3$—DCI): m/z 618 (M+H).

EXAMPLE 104

Preparation of 5-Carboxy-4-[4-(4-acetyl)phenylpiperazin-1-yl]methyl-2-propyl-1-[(2'-(tetrazol-5-yl)biphen-4-yl)methyl]imidazole The title compound was synthesized using the methyl ester obtained from Part B of Example 103 by the procedures outlined in Example 102. $^1$H NMR (300 MHz, DMSO-d$_6$): δ0.84 (t, J=7.3 Hz, 3H); 1.55 (m, 2H); 2.47 (s); 2.56 (t); 3.26 (br s, 4H, piperazine); 3.61 (br s, 4H, piperazine); 4.40 (s, 2H); 5.66 (s, 2H); 6.96-7.08 (m, 6H); 7.52-7.86 (m, 6H). MS (NH$_3$—DCI): m/z 605 (M+H); 561 (M+H—CO$_2$); 518 (M+H—CO$_2$—HN$_3$).

EXAMPLE 105

PART A: Preparation of 5-Methoxycarbonyl-4-[4-(3-trifluoromethylphenyl)-piperazin-1-yl]methyl-2-propyl-1-[(2'-(N-trityltetrazol-5-yl)biphen-4-yl)methyl]imidazole The title compound was synthesized using hydroxymethylimidazole obtained from Part A of Example 101 and 1-(3-trifluoromethylphenyl)piperazine by the method described in Part B of Example 101. $^1$H NMR (300 MHz, CDCl$_3$): δ0.88 (t, J=7.3 Hz, 3H); 1.67 (m, 2H); 2.54 (t, J=7.7 Hz, 2H); 2.76 (br s, 4H, piperazine); 3.27 (br s, 4H, piperazine); 3.72 (s, 3H); 3.90 (s, 2H); 5.43 (s, 2H); 6.74-7.89 (m, 27H). MS (FAB): m/z 887 (M+H); 243 (Tr).

PART B: Preparation of 5-Methoxycarbonyl-4-[4-(3-trifluoromethylphenyl)-piperazin-1-yl]methyl-2-propyl-1-[(2'-(tetrazol-5-yl)biphen-4-yl)methyl]imidazole The title compound was synthesized using the corresponding trityltetrazole analog obtained from Part A of Example 105 by the procedures outlined in Part C of Example 101. $^1$H NMR (300 MHz; DMSO-d$_6$): δ0.88 (t, J=7.3 Hz, 3H); 1.61 (m, 2H); 2.64 (t, J=7.7 Hz, 2H); 3.18 (br s, 4H, piperazine); 3.49 (br s, 4H, piperazine); 3.79 (s, 3H); 4.31 (s, 2H); 5.60 (s, 2H); 6.96-7.68 (m, 12H). MS (NH$_3$—DCI): m/z 645 (M+H). Calculated mass for C$_{34}$H$_{36}$N$_8$O$_2$ (M+H): 645.29133; found: 645.289524.

EXAMPLE 106

Preparation of
5-Carboxy-4-[4-(3-trifluoromethylphenyl)-piperazin-1-yl]methyl-2-propyl-1-[(2'-(tetrazol-5-yl)biphen-4-yl)methyl]imidazole The title compound was synthesized using the methyl ester obtained from Part B of Example 105 by the procedures outlined in Example 102. $^1$H NMR (300 MHz, DMSO-$d_6$): δ0.84 (t, J=7.3 Hz, 3H); 1.55 (m, 2H); 2.54 (t); 3.11 (br s, 4H, piperazine); 3.43 (br s, 4H, piperazine); 4.21 (s, 2H); 5.69 (s, 2H); 6.94–7.70 (m, 12H). MS (NH$_3$—DCI): m/z 631 (M+H); 587 (M+H—CO$_2$). Calculated mass for $C_{33}H_{34}F_3N_8O_2$ (M+H): 631.275682; found: 631.275562.

EXAMPLE 107

PART A: Preparation of
5-Methoxycarbonyl-4-(4-benzylpiperazin-1-yl)methyl-2-propyl-1-[(2'-(N-trityltetrazol-5-yl)biphen-4-yl)methyl]imidazole The title compound was synthesized using the hydroxymethyl imidazole obtained from Part A of Example 101 and 1-benzylpiperazine by the method described in Part B of Example 101. $^1$H NMR (300 MHz, CDCl$_3$): δ0.85 (t, J=7.3 Hz, 3H); 1.64 (m, 2H); 2.51 (t, J=7.7 Hz, 2H); 2.60 (br s); 3.68 (s, 3H); 3.84 (s, 2H); 5.40 (s, 2H); 6.71–7.90 (m, 28H).

PART B: Preparation of
5-Carboxy-4-(4-benzylpiperazin-1-yl)methyl-2-propyl-1-[(2'-(tetrazol-5-yl)biphen-4-yl)methyl]imidazole The title compound was synthesized using the N-trityl methyl ester obtained from Part A of Example 107 by the procedures outlined in Part C of Example 101 substituting 3 N aqueous NaOH for the 5% NaHCO$_3$ solution. $^1$H NMR (300 MHz, DMSO-$d_6$): δ0.82 (t, J=7.3 Hz, 3H); 1.52 (m, 2H); 2.45 (t, J=7.7 Hz, 2H); 2.95 (br s); 3.56 (s, 2H); 4.06 (s, 2H); 5.70 (s, 2H); 7.00 (m, 4H); 7.32 (br s, 5H); 7.50–7.65 (m, 4H). MS(NH$_3$—DCI): m/z 577 (M+H); 533 (M+H—CO$_2$).

EXAMPLE 108

PART A: Preparation of
5-Methoxycarbonyl-4-{4-[phenyl(4-chlorophenyl)-methyl]piperazin-1-yl}methyl-2-propyl-1-[(2'-(N-trityltetrazol-5-yl)biphen-4-yl)methyl]imidazole The title compound was synthesized using the hydroxymethyl imidazole obtained from Part A of Example 101 and 1-(4-chlorobenzhydryl)piperazine by the method described in Part B of Example 101. $^1$H NMR (300 MHz, CDCl$_3$): δ0.84 (t, J=7.3 Hz, 3H); 1.63 (m, 2H); 2.42 (br s); 2.50 (t); 2.61 (br s); 3.67 (s, 3H); 3.82 (s, 2H); 4.19 (s, 1H); 5.40 (s, 2H); 6.71–7.90 (m, 32H). MS (NH$_3$—DCI): m/z 943 (M+H); 887 (M+H—N$_4$).

PART B: Preparation of
5-Carboxy-4-{4-[phenyl(4-chlorophenyl)methyl]-piperazin-1-yl}methyl-2-propyl-1-[(2'-(tetrazol-5-yl)biphen-4-yl)methyl]imidazole The title compound was synthesized using the N-trityl methyl ester obtained from Part A of Example 108 by the procedures outlined in Part B of Example 107. $^1$H NMR (300 MHz, DMSO-$d_6$): δ0.82 (t, J=7.3 Hz, 3H); 1.53 (m, 2H); 2.49 (t); 3.18 (br s); 3.35 (br s); 4.27 (s, 2H); 4.51 (s, 1H); 5.66 (s, 2H); 7.00 (m, 4H); 7.20–7.67 (m, 13H). MS (NH$_3$—DCI): m/z 687 (M+H); 643 (M+H—CO$_2$).

EXAMPLE 109

PART A: Preparation of
5-Methoxycarbonyl-4-[4-(2-trifluoromethylbenzyl)-piperazin-1-yl]methyl-2-propyl-1-[(2'-(N-trityltetrazol-5-yl)biphen-4-yl)methyl]imidazole The title compound was synthesized using the hydroxymethylimidazole obtained from Part A of Example 101 and 1-(2-trifluoromethylbenzyl)piperazine by the method described in Part B of Example 101. $^1$H NMR (300 MHz, CDCl$_3$): δ0.86 (t, J=7.3 Hz, 3H); 1.65 (m, 2H); 2.54 (br t, 6H); 2.63 (br s, 4H); 3.65 (s, 2H); 3.69 (s, 3H); 3.84 (s, 2H); 5.42 (s, 2H); 6.70–7.90 (m, 27H). MS (NH$_3$—CI/DDIP): m/z 901 (M+H); 845 (M+H—N$_4$); 603 (M+H—N$_4$—Tr); 243 (Tr).

PART B: Preparation of
5-Carboxy-4-(2-trifluoromethylbenzyl)-piperazin-1-yl]methyl-2-propyl-1-[(2'-(tetrazol-5-yl)biphen-4-yl)methyl]imidazole The title compound was synthesized using the N-trityl methyl ester obtained from Part A of Example 109 by the procedures outlined in Part B of Example 107. $^1$H NMR (300 MHz, DMSO-$d_6$): δ0.82 (t, J=7.3 Hz, 3H); 1.52 (m, 2H); 2.46 (t, J=7.7 Hz, 2H); 2.98 (br. s); 3.69 (s, 2H); 4.09 (s, 2H); 5.69 (s, 2H); 6.98 (m, 4H); 7.46–7.78 (m, 8H). MS (NH$_3$—DCI): m/z 645 (M+H); 601 (M+H—CO$_2$). Calculated mass for $C_{34}H_{36}N_8O_2F_3$ (M+H): 645.291333; found 645.290121.

EXAMPLE 110

PART A: Preparation of
5-Methoxycarbonyl-4-(3,5-dimethylmorpholin-4-yl)methyl-2-propyl-1-[(2'-(N-trityltetrazol-5-yl)biphen-4-yl)methyl]imidazole The title compound was synthesized using the hydroxymethyl imidazole obtained from Part A of Example 101 and 2,6-dimethylmorpholine by the method described in Part B of Example 101. $^1$H NMR (300 MHz, CDCl$_3$): δ0.86 (t, J=7.3 Hz, 3H); 1.14 (d, J=6.2 Hz, 6H); 1.65 (m, 2H); 1.89 (t, J=11.0 Hz, 2H); 2.53 (t, J=7.7 Hz, 2H); 2.85 (d, J=11.0 Hz, 2H); 3.69 (s, 3H); 3.74 (br, 2H); 3.80 (s, 2H); 5.42 (s, 2H); 6.72–7.90 (m, 23H). MS (NH$_3$—CI/DDIP): m/z 772 (M+H); 716 (M+H—N$_4$); 243 (Tr).

PART B: Preparation of
5-Carboxy-4-(3,5-dimethylmorpholin-4-yl)methyl-2-propyl-1-[(2'-(tetrazol-5-yl)biphen-4-yl)methyl]imidazole The title compound was synthesized using the N-trityl methyl ester obtained from Part A of Example 110 by the procedures outlined in Part B of Example 107. $^1$H NMR (300 MHz, D$_2$O): δ0.57 (t, J=7.3 Hz, 3H); 0.94 (d, J=6.2 Hz, 6H); 1.25 (m, 2H); 1.92 (t, J=11.4 Hz, 2H); 2.34 (t, J=7.7 Hz, 2H); 2.72 (d, J=11.4 Hz, 2H); 3.57 (m, 2H); 3.75 (s, 2H); 5.29 (s, 2H); 6.62–6.79 (m, 4H); 7.21–7.39 (m, 4H).

EXAMPLE 111

PART A: Preparation of 5-Methoxycarbonyl-2-propyl-1-[(2'-(N-trityltetrazol-5-yl)biphen-4-yl)methyl]imidazol-4-carboxaldehyde A suspension of 10.00 g (14.82 mmole) of 5-methoxycarbonyl-4-hydroxy-methyl-2-propyl-1-[(2'-(N-trityltetrazol-5-yl)biphen-4-yl)methyl]imidazole (Example 101, Part A) in 200 mL THF was added to a stirring slurry of 12.88 g (148.2 mmole) of $MnO_2$ at room temperature. The mixture was stirred at room temperature for 2 days. 3.22 g (37.0 mmole) of additional $MnO_2$ was added to the mixture and stirred at room temperature for 5 hours after which TLC (ethyl acetate) showed no starting material. The product was filtered through Celite ™, and the cake was washed with ethyl acetate and methylene chloride; the filtrate was evaporated under reduced pressure to give 8.10 g (81%) of the title compound as a light-yellow-colored solid. $^1H$ NMR (300 MHz, $CDCl_3$): δ0.89 (t, J=7.3 Hz, 3H); 1.74 (m, 2H); 2.58 (t, J=7.7 Hz, 2H); 3.81 (s 3H); 5.49 (s, 2H); 6.74–7.92 (m, 23H); 10.38 (s, 1H). MS ($NH_3$—DCI): m/z 673 (M+H, 10%); 617 (M+H-$N_4$, 100%); 243 (Tr, 20%). Calculated mass for $C_{42}H_{37}N_6O_3$ (M+H): 673.292714; found: 673.292470.

PART B: Preparation of 5-Methoxycarbonyl-4-[4-(3-methoxyphenyl)-piperazin-1-yl]methyl-2-propyl-1-[(2'-(N-trityltetrazol-5-yl)biphen-4-yl)methyl]imidazole To a room temperature suspension of 2.00 g (2.97 mmol) of the imidazole carboxaldehyde obtained from Part A of Example 111 in 25 mL DMF was added sequentially 1.18 g (4.46 mmol) of 1-(3-methoxyphenyl)-piperazine dihydrochloride, 0.85 g (10.4 mmol) of sodium acetate, and 0.26 mL (4.46 mmol) of acetic acid. After stirring for 3 hours, 0.19 g (2.97 mmol) sodium cyanoborohydride was added to the reaction mixture, which was then stirred overnight. Saturated aqueous sodium bicarbonate was added, and the product was extracted with 4×100 mL ethyl acetate. The combined organic layer was washed with 4×200 mL water, 2×100 saturated aqueous ammonium chloride, and 2×100 mL brine, dried over $MgSO_4$, and evaporated under reduced pressure. The crude product was purified by flash chromatography (50–100% ethyl acetate/hexane) to give 1.79 g (70%) of the title compound as a white powder. $^1H$ NMR (300 MHz, $CDCl_3$): δ0.87 (t, J=7.3 Hz, 3H); 1.66 (m, 2H); 2.54 (t, J=7.7 Hz, 2H); 2.78 (br s, 4H); 3.24 (br s, 4H); 3.71 (s, 3H); 3.78 (s, 3H); 3.92 (s, 2H); 5.45 (s, 2H); 6.39–7.89 (m, 27H). MS (FAB): m/z 849 (M+H); 607 (M+H—Tr); 243 (Tr).

PART C: Preparation of 5-Carboxy-4-[4-(3-methoxyphenyl)-piperazin-1-yl]methyl-2-propyl-1-[(2'-(tetrazol-5-yl)biphen-4-yl)methyl]imidazole The title compound was synthesized using the trityltetrazole-methyl ester obtained from Part B of Example 111 by the procedures outlined in Part B of Example 107. $^1H$ NMR (300 MHz, DMSO-$d_6$): δ0.84 (t, J=7.3 Hz, 3H); 1.55 (m, 2H); 2.51 (t); 3.10 (br s, 4H); 3.32 (br. s, 4H); 3.72 (s, 3H); 4.29 (s, 2H); 5.69 (s, 2H); 6.42–7.69 (m, 12H). MS (FAB-NBA): m/z 593 (M+H); 615 (M+Na). Calculated mass for $C_{33}H_{37}N_8O_3$ (M+H): 593.298863; found: 593.298632.

EXAMPLE 112

PART A: Preparation of 5-Methoxycarbonyl-4-[4-(2-pyrimidinyl)-piperazin-1-yl]methyl-2-propyl-1-[(2'-(N-trityltetrazol-5-yl)biphen-4-yl)methyl]imidazole The title compound was synthesized using the imidazole carboxaldehyde obtained from Part A of Example 111 and 1-(2-pyrimidyl)piperazine dihydrochloride by the method described in Part B of Example 111. $^1H$ NMR (300 MHz, $CDCl_3$): δ0.86 (t, J=7.3 Hz, 3H); 1.62 (m); 2.53 (t, J=7.7 Hz, 2H); 2.65 (br t, 4H); 3.70 (s, 3H); 3.85 (br t, 4H); 3.88 (s, 2H); 5.42 (s, 2H); 6.43–8.29 (m, 26H). MS ($NH_3$—DCI): m/z 821 (M+H); 765 (M+H—$N_4$).

PART B: Preparation of 5-Carboxy-4-[4-(2-pyrimidinyl)-piperazin-1-yl]methyl-2-propyl-1-[(2'-(tetrazol-5-yl)biphen-4-yl)methyl]imidazole The title compound was synthesized using the trityltetrazole-methyl ester obtained from Part A of Example 112 by the procedures outlined in Part B of Example 107. $^1H$ NMR (300 MHz, DMSO-$d_6$): δ0.83 (t, J=7.3 Hz, 3H); 1.55 (m, 2H); 2.53 (t); 3.09 (br s, 4H); 3.92 (br s, 4H); 4.23 (s, 2H); 5.67 (s, 2H); 6.73 (t, J=4.8 Hz, 1H); 6.96–7.05 (m, 4H); 7.52–7.68 (m, 4H); 8.42 (d, J=4.8 Hz, 2H). MS ($NH_3$—DCI): m/z 565 (M+H); 521 (M+H—$CO_2$). Calculated mass for $C_{30}H_{33}N_{10}O_2$ (M+H): 565.278796; found: 565.279678.

EXAMPLE 113

PART A: Preparation of 5-Methoxycarbonyl-4-[4-(2-chlorophenyl)-piperazin-1-yl]methyl-2-propyl-1-[(2'-(N-trityltetrazol-5-yl)biphen-4-yl)methyl]imidazole The title compound was synthesized using the imidazole carboxaldehyde obtained from Part A of Example 111 and 1-(2-chlorophenyl)piperazine monohydrochloride by the method described in Part B of Example 111. $^1H$ NMR (300 MHz, $CDCl_3$): δ0.88 (t, J=7.3 Hz, 3H); 1.67 (m, 2H); 2.54 (t, J=7.7 Hz, 2H); 2.83 (br s, 4H); 3.13 (br s, 4H); 3.72 (s, 3H); 3.94 (s, 2H); 5.43 (s, 2H); 6.74–7.90 (m, 27 H). MS (FAB): m/z 853 (M+H); 611 (M+H—Tr); 243 (Tr).

PART B: Preparation of 5-Carboxy-4-[4-(2-chlorophenyl)-piperazin-1-yl]methyl-2-propyl-1-[(2'-(tetrazol-5-yl)biphen-4-yl)methyl]imidazole The title compound was synthesized using the trityltetrazole-methyl ester obtained from Part A of Example 113 by the procedures outlined in Part B of Example 107. $^1H$ NMR (300 MHz, DMSO-$d_6$): δ0.85 (t, J=7.3 Hz, 3H); 1.57 (m, 2H); 2.55 (t, J=7.7 Hz, 2H); 3.25 (br); 4.36 (s, 2H); 5.68 (s, 2H); 6.96–7.70 (m, 12H). MS (FAB-NBA): m/z 597 (M+H); 619 (M+Na). Calculated mass for $C_{32}H_{34}N_8O_2Cl$ (M+H): 597.249325; found 597.250772.

EXAMPLE 114

PART A: Preparation of 4,5-Bis(methoxycarbonyl)-1-(4-bromophenyl)methyl-2-propylimidazole A solution of 40.0 g (0.177 mole) of 2-propyl-4,5-bis(methoxycarbonyl)-imidazole and 44.6 g (0.178 mole) of 4-bromobenzyl bromide in 350 mL of DMF was stirred in the presence of 37.5 g (0.271 mole) of $K_2CO_3$ overnight at room temperature. The reaction mixture was then poured into 1200 mL of water and extracted with 3×300 mL of ether. The combined ether extracts were washed with 8×1000 mL of water and once with brine, then dried over $MgSO_4$. The solvent was removed under reduced pressure to yield 61.8 g (88%) of the title compound as a solid. $^1H$ NMR (300 MHz, $CDCl_3$): δ0.94 (t, J=7.6 Hz, 3H); 1.73 (m, 2H); 2.63 (t, J=7.9 Hz, 2H); 3.81 (s, 3H); 3.93 (s, 3H); 5.37 (s, 2H); 6.86 (d, J=8.8 Hz, 2H); 7.45 (d, J=8.8 Hz, 2H). MS [DCI ($NH_3$)]: m/z 395/397 (M+H, 1 Br).

PART B: Preparation of 5-Methoxycarbonyl-1-(4-bromophenyl)methyl-2-propyl-4-hydroxymethylimidazole The imidazole diester prepared in Example 114, Part A was reduced with DIBAL-H following the procedure of Example 101, Part A, except the workup was modified. When TLC (ethyl acetate) showed the disappearance of starting material, the reaction mixture was poured into a chilled, saturated solution of sodium potassium tartrate. The organic layer was separated, and the aqueous layer was extracted twice with ethyl acetate. The combined organic layers were washed in turn with saturated $NaHCO_3$ and 2× brine, and dried over anhydrous $MgSO_4$. The solvents were then removed under reduced pressure to yield the title compound in 98% yield. $^1H$ NMR (300 MHz, $CDCl_3$): δ0.95 (t, J=7.4 Hz, 3H); 1.74 (m, 2H); 2.60 (t, J=7.7 Hz, 2H); 3.47 (t, J=6.1 Hz, 1H); 3.80 (s, 3H); 4.83 (d, J=6.1 Hz, 2H); 5.47 (s, 2H); 6.85 (d, J=8.6 Hz, 2H); 7.44 (d, J=8.6 Hz, 2H). MS [DCI ($NH_3$)]: m/z 367/369 (M+H, 1 Br).

PART C: Preparation of 5-Methoxycarbonyl-1-(4-bromophenyl)methyl-2-propyl-4-([4-(2-pyridyl)-piperazin-1-yl]methyl)imidazole The title compound was prepared in 38% yield by the procedure used in Example 101, Part B. $^1H$ NMR (300 MHz, $CDCl_3$): δ0.93 (t, 3H, J=7.0 Hz); 1.71 (m, 2H); 2.63 (t, 3H, J=8.0 Hz); 2.70 (m, 4H); 3.57 (m, 4H); 3.78 (s, 3H); 3.88 (s, 2H); 5.47 (s, 2H); 6.62 (m, 2H); 6.83 (d, 2H, J=8.1 Hz); 7.44 (m, 3H); 8.18 (d, $^1H$, J=4.0 Hz). MS [DCI ($NH_3$)]: m/z 512/514 (M+H, 1 Br).

PART D: Preparation of 2-((t-butylamino)sulfonyl)phenyl boronic acid

To a 0° C. solution of 34.0 g (0.160 mol) of benzene-N-(t-butyl)sulfon-amide in 500 mL of THF under $N_2$ was added 160 mL (0.360 mol) of 2.25M n-butyllithium in hexanes over 35 min., keeping the temperature between 0°–2° C. The reaction mixture was allowed to warm to room temperature over 1.5 h, during which time a thick precipitate formed. Triisopropylborate (46 mL, 0.20 mol) was added, keeping the temperature below 35° C. After 1 h, the reaction mixture was cooled, 1N HCl (260 mL) was added, and the mixture was stirred 30 min. After diluting with 520 mL of $H_2O$, the mixture was extracted with 3×400 mL of ether. The combined organic extracts were extracted with 3×200 mL of 1N NaOH, and the aqueous extracts were acidified to pH 1 with 6N HCl, then extracted with 3×250 mL of ether. The ether extracts were washed with 250 mL of brine, dried ($MgSO_4$) and the solvents were removed under reduced pressure to give 45 g of a thick oil. After addition of toluene (45 mL), the mixture was agitated for 1 h on the rotovap. A small quantity of solid formed, which was used to induce partial solidification of the remaining crude product. Additional toluene (150 mL) was added, and the mixture was reduced to ½ volume under reduced pressure, keeping the temperature from 0°–10° C. The resulting precipitate was collected and washed with hexane, then dried under vacuum to give 24.6 g (60%) of the title compound as small white crystals, m.p. 118°–119° C. $^1H$ NMR (300 MHz, $CDCl_3$): δ1.18 (s, 9H); 6.29 (br s, 2H); 7.53 (m, 2H); 7.82 (I, J=7.2 Hz; 1H); 8.00 (I, J=7.5 Hz, 1H).

PART E: Preparation of 5-Methoxycarbonyl-1-[2'-((t-butylamino)sulfonyl)biphen-4-yl]methyl-2-propyl-4-([4-(2-pyridyl)-piperazin-1-yl]methyl)imidazole A mixture of 0.92 g (1.80 mmole) of the bromobenzylimidazole prepared in Example 114, Part C, 0.46 g (1.80 mmole) 2-((t-butylamino)sulfonyl)phenyl boronic acid (Example 114, Part D), 0.06 g (0.019 mmole) tetrabutylammonium bromide, and 0.50 g (3.62 mmole) potassium carbonate in 1 mL of water and 9 mL of toluene was degassed and placed under a nitrogen atmosphere. To this mixture was added 0.10 g (0.087 mmole) of tetrakis(triphenylphosphine)-palladium and the degassing procedure repeated. The reaction mixture was refluxed overnight, cooled, diluted to 25 mL with toluene and washed with 50 mL water. The aqueous layer was washed an additional two times with 25 mL of toluene. The combined toluene layers were washed twice with 25 mL of water, 2×25 mL of brine, and dried over anhydrous $MgSO_4$. The toluene was removed under reduced pressure to give 1.09 g of crude product which was purified by silica gel flash chromatography (0–5% methanol in ethyl acetate) to give 0.79 g (68%) of the title compound. $^1H$ NMR (300 MHz, $CDCl_3$): δ0.97 (s, 9H); 0.97 (t, J=7.7 Hz, 3H); 1.73 (m, 2H); 2.67 (t, J=7.7 Hz, 2H); 2.74 (m, 4H); 3.46 (s, 1H); 3.60 (m, 4H); 3.80 (s, 3H); 3.93 (s, 2H); 5.59 (s, 2H); 6.62 (m, 2H); 7.05 (d, J=8.1 Hz, 2H) 7.46 (m, 5H); 8.18 (m, 2H). MS [DCI ($NH_3$)]: m/z 645 (M+H).

PART F: Preparation of 5-Methoxycarbonyl-1-[[(2'-aminosulfonyl)biphen-4-yl]methyl]-2-propyl-4-([4-(2-pyridyl)-piperazin-1-yl]methyl)imidazole A solution of 0.79 g (1.24 mmole) of the product of Example 114, Part E in 10 mL of trifluoroacetic acid was refluxed for one hour. After the excess trifluoroacetic acid was removed under reduced pressure, the residue was taken up in 150 mL of dichloromethane and washed with 50 mL of 5% $NaHCO_3$. The bicarbonate wash was washed with 2×25 mL of dichloromethane. The combined organic layers were washed with brine and dried over anhydrous $MgSO_4$. The solvent was removed under reduced pressure to give 0.68 g (94%) of the title compound as a white solid. $^1H$ NMR (300 MHz, $CDCl_3$): δ0.96 (t, J=7.3 Hz, 3H); 1.72 (m, 2H); 2.69 (m, 6H); 3.58 (m, 4H); 3.80 (s, 3H); 3.90 (s, 2H); 4.17 (s, 2H); 5.59 (s, 2H); 6.62 (m, 2H); 7.07 (d, J=8.1 Hz, 2H); 7.30–7.60 (m, 6H); 8.16 (m, 2H). MS [DCI ($NH_3$)]: m/z 589 (M+H).

PART G: Preparation of 5-Methoxycarbonyl-1-[[2'-(N-cyclopropylcarbonyl)sulfonamidobiphen-4-yl]methyl]-2-propyl-4-([4-(2-pyridyl)-piperazin-1-yl]methyl)imidazole A solution of 0.282 g (1.74 mmole) of carbonyldiimidazole and 140 mL (0.152 g) of cyclopropane carboxylic acid in 2.5 mL anhydrous THF was refluxed for two hours and then cooled to room temperature. To this was added a solution of 0.34 g (0.58 mmole) of the sulfonamide prepared in Example 114, Part F and 265 ml (1.74 mmole) of DBU. The reaction mixture refluxed for 1.5 hours, then stirred at room temperature overnight. The reaction mixture was poured into 10 mL of 25% citric acid and extracted twice with 10 mL of ethyl acetate. The citric acid solution was then brought to a pH of 4–5 depositing a gummy residue which was washed with water by decantation twice and then dissolved in methanol. The decanted citric acid solution was extracted three times with 10 mL of ethyl acetate. The ethyl acetate extracts were combined with the methanol solution and stripped under reduced pressure to give 0.37 g (0.56 mmole, 97.4%) of title compound which contained a trace of non-acylated sulfonamide (TLC, 20% methanol/80% ethyl acetate). $^1$H NMR (300 MHz, CDCl$_3$): δ0.59 (m, 3H); 0.88 (t, J=7.7 Hz, 3H); 1.25 (m, 1 H); 1.65 (m, 2H); 2.63 (m,4H); 3.48 (m, 4H); 3.76 (s, 3H); 3.83 (s, 2H); 5.62 (s, 2H); 6.62 (m, 1H); 6.80 (d, J=8.7 Hz, 1H); 7.00 (d, J=8.0 Hz, 2H); 7.25 (t, J=6.2 Hz, 3H); 7.56 (m, H); 8.03 (d, J=7.6 Hz, 1H); 8.09 (d, J=4.8 Hz, 1H). MS [DCI (NH$_3$)]: m/z 657 (M+H).

EXAMPLE 115

Preparation of 1-[[2'-(N-cyclopropylcarbonyl)sulfonamidobiphen-4-yl]methyl]-2-propyl-4-[4-(2-pyridyl)-piperazin-1-yl]methylimidazol-5-carboxylic acid A solution of the imidazole methyl ester prepared in Example 114, Part G was prepared by dissolving 0.33 g (0.50 mmoles) in 50 mL of methanol, adding 15 mL of 5% NaHCO$_3$ and removing the methanol under reduced pressure. The aqueous solution obtained was washed twice with ethyl acetate and filtered. To this solution was added 20 mL of 1N NaOH and the reaction mixture stirred at room temperature overnight. The next day the reaction mixture was again filtered and the pH was adjusted to pH 6–7 with 6N hydrochloric acid. The resulting white precipitate was filtered, washed twice with water, and dried under reduced pressure to give 0.13 g (39%) of the title compound. 1H NMR (300 MHz, CDCl$_3$): δ0.75 (m, 2H); 0.90 (m, 2H); 1.00 (t, J=7.4 Hz, 3H); 1.42 (m, 1H); 1.80 (m, 2H); 2.71 (t, J=7.3 Hz, 2H); 3.25 (br s, 4H, piperazine); 4.02 (s, 2H); 4.30 (br s, 4H, piperazine); 5.65 (s, 2H); 6.68 (m, 2H); 7.01 (d, J=8.0 Hz, 2H); 7.26 (m, 3H); 7.58 (m, 3H); 8.10 (d, J=5.0 Hz, $^1$H); 8.38 (d, J=8.0 Hz, $^1$H). MS [DCI (NH$_3$)]: m/z 643 (M+H); 599 (M+H—CO$_2$).

EXAMPLE 116

Preparation of 5-Methoxycarbonyl-1-[(2'-(N-benzoyl)sulfonamidobiphen-4-yl)methyl]-2-propyl-4-([4-(2-pyridyl)-piperazin-1-yl)methyl)imidazole The title compound was prepared in 72% yield using the procedure described in Example 114, Part G. $^1$H NMR (300 MHz, CDCl$_3$): δ0.90 (t, J=7.3 Hz, 3H); 1.67 (m, 2H); 2.57 (t, 2H, J=7.0 Hz); 2.80 (br s, 4H, piperazine); 3.55 (br s, 4H, piperazine); 3.78 (s, 2H); 4.00 (s, 1H); 5.56 (s, 2H); 6.65 (m, 1H); 6.83 (d, J=8.0 Hz, 2H); 7.12-7.64 (m,12H); 8.10 (m, 2H). MS [DCI (NH$_3$)]: m/z 693 (M+H); 510 (M+H—R; R =C$_6$H$_5$CONHSO$_2$H).

EXAMPLE 117

Preparation of 1-([(2'-(N-benzoyl)sulfonamidoyl)biphen-4-yl]methyl)-2-propyl-4-[4-(2-pyridyl)-piperazin-1-yl)methylimidazol-5-carboxylic acid The title compound was prepared in 22% yield using the procedure similar of Example 115. $^1$H NMR (300 MHz, CDCl$_3$): δ0.97 (t, J=7.3 Hz, 3H); 1.73 (m, 2H); 2.60 (t, J=7.3 Hz, 2H); 2.75 (s, broad, 2H); 3.20 (br s, 2H, piperazine); 4.02 (s, 2H); 4.25 (br s, 4H, piperazine); 5.68 (s, 2H); 6.65 (m, 2H); 6.87 (d, J=8.0, 2H); 7.24 (m, 3H); 7.44-7.64 (m, 8H); 8.20 (d, J=3.7 Hz, 1H); 8.39 (d, J=7.0 Hz, 1H). MS [DCI (NH$_3$)]: m/z 679 (M+H); 635 (M+H—CO$_2$).

Using the procedures of Examples 101–117 and Scheme II, and the references above, the following Formula (I) compounds of Table 2 may be prepared:

TABLE 2

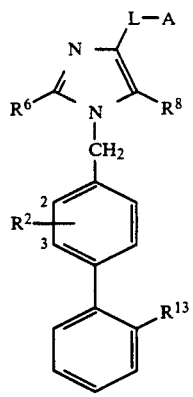

| Ex. No. | $R^2$ | $R^6$ | $R^8$ | L | A | $R^{13}$ | m.p. |
|---|---|---|---|---|---|---|---|
| 101 | H | n-C$_3$H$_7$ | CO$_2$CH$_3$ | CH$_2$ | 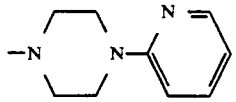 | tetrazol-5-yl | a. |

TABLE 2-continued

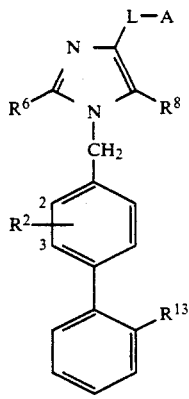

| Ex. No. | R² | R⁶ | R⁸ | L | A | R¹³ | m.p. |
|---|---|---|---|---|---|---|---|
| 102 | H | n-C₃H₇ | CO₂H | CH₂ | -N(piperazin-1-yl)-2-pyridyl | tetrazol-5-yl | a. |
| 103 | H | n-C₃H₇ | CO₂CH₃ | CH₂ | 4-(4-acetylphenyl)-piperazin-1-yl | tetrazol-5-yl | a. |
| 104 | H | n-C₃H₇ | CO₂H | CH₂ | 4-(4-acetylphenyl)-piperazin-1-yl | tetrazol-5-yl | a. |
| 105 | H | n-C₃H₇ | CO₂CH₃ | CH₂ | 4-[3-(CF₃)-phenyl]-piperazin-1-yl | tetrazol-5-yl | a. |
| 106 | H | n-C₃H₇ | CO₂H | CH₂ | 4-[3-(CF₃)-phenyl]-piperazin-1-yl | tetrazol-5-yl | a. |
| 107 | H | n-C₃H₇ | CO₂H | CH₂ | -N(piperazinyl)NCH₂Ph | tetrazol-5-yl | a. |
| 108 | H | n-C₃H₇ | CO₂H | CH₂ | -N(piperazinyl)NCH(p-Cl—Ph)Ph | tetrazol-5-yl | a. |
| 109 | H | n-C₃H₇ | CO₂H | CH₂ | 4-[2-(CF₃)-benzyl]-piperazin-1-yl | tetrazol-5-yl | a. |
| 110 | H | n-C₃H₇ | CO₂H | CH₂ | -N(2,6-dimethylmorpholin-4-yl) | tetrazol-5-yl | a. |
| 111 | H | n-C₃H₇ | CO₂H | CH₂ | 4-[3-(CH₃O)-phenyl]-piperazin-1-yl | tetrazol-5-yl | a. |
| 112 | H | n-C₃H₇ | CO₂H | CH₂ | -N(piperazin-1-yl)-2-pyrimidinyl | tetrazol-5-yl | a. |
| 113 | H | n-C₃H₇ | CO₂H | CH₂ | -N(piperazin-1-yl)-(2-Cl-phenyl) | tetrazol-5-yl | a. |

TABLE 2-continued

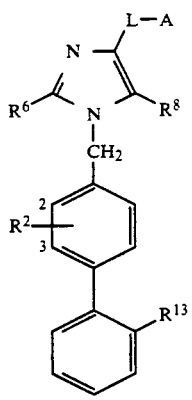

| Ex. No. | R² | R⁶ | R⁸ | L | A | R¹³ | m.p. |
|---|---|---|---|---|---|---|---|
| 114 | H | n-C₃H₇ | CO₂CH₃ | CH₂ | -N(piperazinyl)-pyridin-2-yl | -SO₂-NH-C(O)-cyclopropyl | a. |
| 115 | H | n-C₃H₇ | CO₂H | CH₂ | -N(piperazinyl)-pyridin-2-yl | -SO₂-NH-C(O)-cyclopropyl | a. |
| 116 | H | n-C₃H₇ | CO₂CH₃ | CH₂ | -N(piperazinyl)-pyridin-2-yl | -SO₂-NH-C(O)-Ph | a. |
| 117 | H | n-C₃H₇ | CO₂H | CH₂ | -N(piperazinyl)-pyridin-2-yl | -SO₂-NH-C(O)-Ph | a. |
| 118 | H | n-C₃H₇ | CHO | CH₂ | -N(piperazinyl)-pyridin-2-yl | tetrazol-5-yl | b. |
| 119 | H | n-C₃H₇ | CH₂OH | CH₂ | -N(piperazinyl)-pyridin-2-yl | tetrazol-5-yl | c. |
| 120 | H | n-C₃H₇ | CH=CHCO₂H | CH₂ | -N(piperazinyl)-pyridin-2-yl | tetrazol-5-yl | |
| 121 | H | n-C₃H₇ | CH₂OCH₃ | CH₂ | -N(piperazinyl)-pyridin-2-yl | tetrazol-5-yl | |
| 122 | 2-F | n-C₃H₇ | CO₂H | CH₂ | -N(piperazinyl)-pyridin-2-yl | tetrazol-5-yl | d. |

TABLE 2-continued

Structure: imidazole with R⁶ at 2-position, L—A at 4-position, R⁸ at 5-position, N1 connected via CH₂ to biphenyl bearing R² (at 2 or 3) and R¹³ (ortho on second ring).

| Ex. No. | R² | R⁶ | R⁸ | L | A | R¹³ | m.p. |
|---|---|---|---|---|---|---|---|
| 123 | 2-Cl | n-C₃H₇ | CO₂H | CH₂ | -N(piperazinyl)-2-pyridyl | tetrazol-5-yl | |
| 124 | 2-Br | n-C₃H₇ | CO₂H | CH₂ | -N(piperazinyl)-2-pyridyl | tetrazol-5-yl | |
| 125 | 2-Me | n-C₃H₇ | CO₂H | CH₂ | -N(piperazinyl)-2-pyridyl | tetrazol-5-yl | i. |
| 126 | 2-MeO | n-C₃H₇ | CO₂H | CH₂ | -N(piperazinyl)-2-pyridyl | tetrazol-5-yl | |
| 127 | 2-CF₃ | n-C₃H₇ | CO₂H | CH₂ | -N(piperazinyl)-2-pyridyl | tetrazol-5-yl | |
| 128 | H | n-C₃H₇ | CO₂H | CH₂CH₂ | -N(piperazinyl)-2-pyridyl | tetrazol-5-yl | |
| 129 | H | n-C₃H₇ | CO₂H | COCH₂ | -N(piperazinyl)-2-pyridyl | tetrazol-5-yl | |
| 130 | H | n-C₃H₇ | CO₂H | (CH₂)₃ | -N(piperazinyl)-2-pyridyl | tetrazol-5-yl | |
| 131 | H | n-C₃H₇ | CO₂H | (CH₂)₄ | -N(piperazinyl)-2-pyridyl | tetrazol-5-yl | |
| 132 | H | n-C₃H₇ | CO₂H | (CH₂)₅ | -N(piperazinyl)-2-pyridyl | tetrazol-5-yl | |

TABLE 2-continued

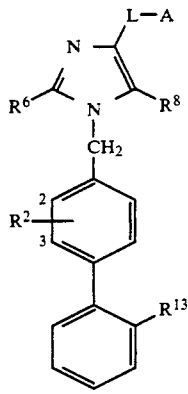

| Ex. No. | $R^2$ | $R^6$ | $R^8$ | L | A | $R^{13}$ | m.p. |
|---|---|---|---|---|---|---|---|
| 133 | H | n-$C_3H_7$ | $CO_2H$ | $(CH_2)_6$ | —N(piperazinyl)-2-pyridyl | tetrazol-5-yl | |
| 134 | H | n-$C_3H_7$ | $CO_2H$ | $(CH_2)_7$ | —N(piperazinyl)-2-pyridyl | tetrazol-5-yl | |
| 135 | H | n-$C_3H_7$ | $CO_2H$ | $(CH_2)_8$ | —N(piperazinyl)-2-pyridyl | tetrazol-5-yl | |
| 136 | H | n-$C_3H_7$ | $CO_2H$ | CH=CHCH$_2$ | —N(piperazinyl)-2-pyridyl | tetrazol-5-yl | |
| 137 | H | n-$C_3H_7$ | $CO_2H$ | —C≡C—CH$_2$ | —N(piperazinyl)-2-pyridyl | tetrazol-5-yl | |
| 138 | H | n-$C_3H_7$ | $CO_2H$ | —CH$_2$N(Ac)—(CH$_2$)$_2$ | —N(piperazinyl)-2-pyridyl | tetrazol-5-yl | |
| 139 | H | n-$C_3H_7$ | $CO_2H$ | CH$_2$O(CH$_2$)$_2$ | —N(piperazinyl)-2-pyridyl | tetrazol-5-yl | |
| 140 | H | n-$C_3H_7$ | $CO_2H$ | CH$_2$S(CH$_2$)$_2$ | —N(piperazinyl)-2-pyridyl | tetrazol-5-yl | |
| 141 | H | n-$C_3H_7$ | $CO_2H$ | CH$_2$SO(CH$_2$)$_2$ | —N(piperazinyl)-2-pyridyl | tetrazol-5-yl | |
| 142 | H | n-$C_3H_7$ | $CO_2H$ | CH$_2$SO$_2$(CH$_2$)$_2$ | —N(piperazinyl)-2-pyridyl | tetrazol-5-yl | |

TABLE 2-continued

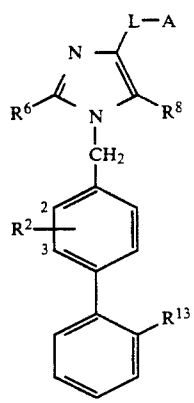

| Ex. No. | R² | R⁶ | R⁸ | L | A | R¹³ | m.p. |
|---|---|---|---|---|---|---|---|
| 143 | H | n-C₃H₇ | CO₂H | CH₂ | -N(piperazinyl)-2-pyridyl | NHSO₂CF₃ | |
| 144 | H | n-C₃H₇ | CO₂H | CH₂ | -N(piperazinyl)-2-pyridyl | NHCOCF₃ | |
| 145 | H | n-C₃H₇ | CO₂H | CH₂ | -N(piperazinyl)-2-pyridyl | CO₂H | |
| 146 | H | n-C₃H₇ | CO₂H | CH₂ | -N(piperazinyl)-N-n-Bu | NHSO₂C(O)Ph | |
| 147 | H | n-C₃H₇ | CO₂H | CH₂ | -N(piperazinyl)-Ph | NHSO₂C(O)Ph | |
| 148 | H | n-C₃H₇ | CO₂H | CH₂ | -N(piperazinyl)-Ph | NHSO₂C(O)-cyclopropyl | |
| 149 | H | n-C₃H₇ | CO₂H | CH₂ | -N(piperazinyl)-2-pyridyl | NHSO₂C(O)-n-Pr | |
| 150 | H | n-C₃H₇ | CO₂H | CH₂ | -N(piperazinyl)-2-pyridyl | NHC(O)NHSO₂CH₃ | |
| 151 | H | n-C₃H₇ | CO₂H | CH₂ | -N(piperazinyl)-2-pyridyl | NHSO₂NHC(O)Ph | |

TABLE 2-continued
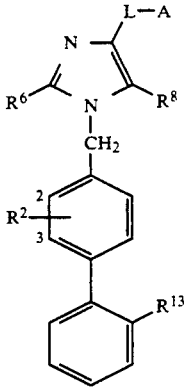
| Ex. No. | R² | R⁶ | R⁸ | L | A | R¹³ | m.p. |
|---|---|---|---|---|---|---|---|
| 152 | H | n-C₃H₇ | CO₂H | CH₂ | 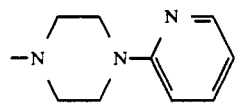 | 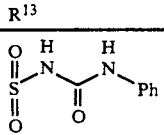 | |
| 153 | H | n-C₃H₇ | CO₂H | CH₂ | 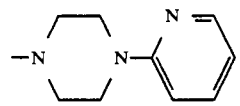 | 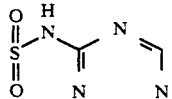 | |
| 154 | H | C₂H₅ | CO₂H | CH₂ | 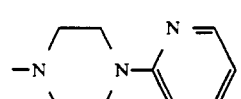 | tetrazol-5-yl | e. |
| 155 | H | n-C₄H₉ | CO₂H | CH₂ | 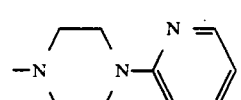 | tetrazol-5-yl | |
| 156 | H | n-C₄H₉ | CO₂H | CH₂ | 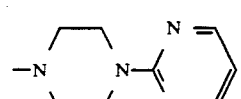 | tetrazol-5-yl | |
| 157 | H | C₂H₅ ⟍⟋ | CO₂H | CH₂ | 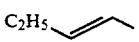 | tetrazol-5-yl | |
| 158 | H | n-C₃H₇ | CO₂H | CH₂ | 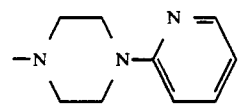 | tetrazol-5-yl | |
| 159 | H | n-C₃H₇ | CO₂H | CH₂ | 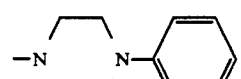 | tetrazol-5-yl | |
| 160 | H | n-C₃H₇ | CO₂H | CH₂ |  | tetrazol-5-yl | |

TABLE 2-continued

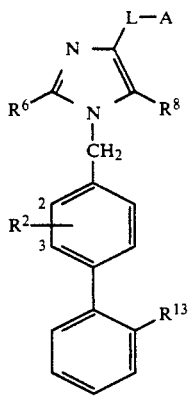

| Ex. No. | R² | R⁶ | R⁸ | L | A | R¹³ | m.p. |
|---|---|---|---|---|---|---|---|
| 161 | H | n-C₃H₇ | CO₂H | CH₂ | -N(piperazine with CH₂Ph)-pyridin-2-yl | tetrazol-5-yl | |
| 162 | H | n-C₃H₇ | CO₂H | CH₂ | -N(piperazine with CH₂Ph)-phenyl | tetrazol-5-yl | |
| 163 | H | n-C₃H₇ | CO₂H | CH₂ | -N(piperazine with Ph)-phenyl | tetrazol-5-yl | |
| 164 | H | n-C₃H₇ | CO₂H | CH₂ | -N(piperazine with CH₃)-phenyl | tetrazol-5-yl | |
| 165 | H | n-C₃H₇ | CO₂H | CH₂ | -N(piperazine with CH₃)-(3-CH₃-phenyl) | tetrazol-5-yl | f. |
| 166 | H | n-C₃H₇ | CO₂H | CH₂ | -N(piperazine with n-Bu)-phenyl | tetrazol-5-yl | |
| 167 | H | n-C₃H₇ | CO₂H | CH₂ | -N(piperazine with n-C₅H₁₁)-phenyl | tetrazol-5-yl | |

TABLE 2-continued
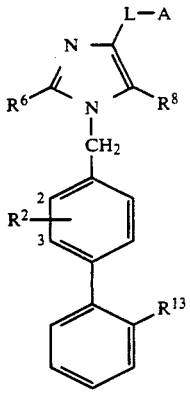
| Ex. No. | R² | R⁶ | R⁸ | L | A | R¹³ | m.p. |
|---|---|---|---|---|---|---|---|
| 168 | H | n-C₃H₇ | CO₂H | CH₂ | 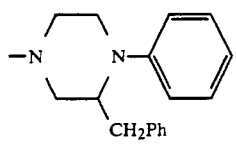 | tetrazol-5-yl | |
| 169 | H | n-C₃H₇ | CO₂H | CH₂ | 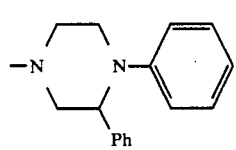 | tetrazol-5-yl | |
| 170 | H | n-C₃H₇ | CO₂H | CH₂ | 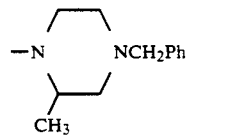 | tetrazol-5-yl | |
| 171 | H | n-C₃H₇ | CO₂H | CH₂ | 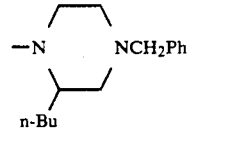 | tetrazol-5-yl | |
| 172 | H | n-C₃H₇ | CO₂H | CH₂ | 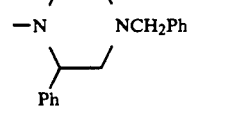 | tetrazol-5-yl | |
| 173 | H | n-C₃H₇ | CO₂H | CH₂ | 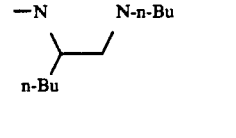 | tetrazol-5-yl | |
| 174 | H | n-C₃H₇ | CO₂H | CH₂ | 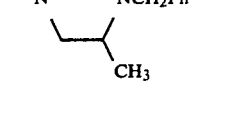 | tetrazol-5-yl | |

TABLE 2-continued

Structure: imidazole with L-A at position, R6, R8, N-CH2-biphenyl with R2 and R13

| Ex. No. | R² | R⁶ | R⁸ | L | A | R¹³ | m.p. |
|---|---|---|---|---|---|---|---|
| 175 | H | n-C$_3$H$_7$ | CO$_2$H | CH$_2$ | piperazinyl with NCH$_2$Ph and n-Bu substituents | tetrazol-5-yl | |
| 176 | H | n-C$_3$H$_7$ | CO$_2$H | CH$_2$ | piperazinyl with NCH$_2$Ph and Ph substituents | tetrazol-5-yl | |
| 177 | H | n-C$_3$H$_7$ | CO$_2$H | CH$_2$ | piperazinyl with N-n-Bu and n-Bu substituents | tetrazol-5-yl | |
| 178 | H | n-C$_3$H$_7$ | CO$_2$H | CH$_2$ | piperazinyl-N-(4-fluorophenyl) | tetrazol-5-yl | |
| 179 | H | n-C$_3$H$_7$ | CO$_2$H | CH$_2$ | piperazinyl-N-(4-methylphenyl) | tetrazol-5-yl | |
| 180 | H | n-C$_3$H$_7$ | CO$_2$H | CH$_2$ | piperazinyl-N-(pyridin-3-yl) | tetrazol-5-yl | |
| 181 | H | n-C$_3$H$_7$ | CO$_2$H | CH$_2$ | piperazinyl-N-(pyridin-4-yl) | tetrazol-5-yl | |
| 182 | H | n-C$_3$H$_7$ | CO$_2$H | CH$_2$ | piperazinyl-N-(pyrazin-2-yl) | tetrazol-5-yl | |
| 183 | H | n-C$_3$H$_7$ | CO$_2$H | CH$_2$ | piperazinyl-N-(1,3,5-triazin-2-yl) | tetrazol-5-yl | |

TABLE 2-continued

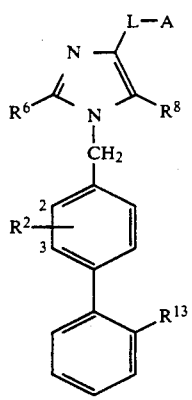

| Ex. No. | R² | R⁶ | R⁸ | L | A | R¹³ | m.p. |
|---|---|---|---|---|---|---|---|
| 184 | H | n-C₃H₇ | CO₂H | CH₂ | 4-(oxazol-2-yl)piperazin-1-yl | tetrazol-5-yl | |
| 185 | H | n-C₃H₇ | CO₂H | CH₂ | 4-(thiazol-2-yl)piperazin-1-yl | tetrazol-5-yl | |
| 186 | H | n-C₃H₇ | CO₂CH₃ | CH₂ | 4-(thien-2-yl)piperazin-1-yl | tetrazol-5-yl | |
| 187 | H | n-C₃H₇ | CO₂H | CH₂ | 4-benzoylpiperazin-1-yl | tetrazol-5-yl | |
| 188 | H | n-C₃H₇ | CO₂H | CH₂ | 4-(diphenylacetyl)piperazin-1-yl | tetrazol-5-yl | |
| 189 | H | n-C₃H₇ | CO₂H | CH₂ | 4-(isobutoxycarbonyl)piperazin-1-yl | tetrazol-5-yl | |
| 190 | H | n-C₃H₇ | CO₂H | CH₂ | 4-(N,N-di-n-butylcarbamoyl)piperazin-1-yl | tetrazol-5-yl | |
| 191 | 2-F | n-C₃H₇ | CO₂H | CH₂ | 2,6-dimethylmorpholin-4-yl | tetrazol-5-yl | g. |
| 192 | H | n-C₃H₇ | CO₂H | CH₂ | thiomorpholin-4-yl | tetrazol-5-yl | h. |

TABLE 2-continued

| Ex. No. | R² | R⁶ | R⁸ | L | A | R¹³ | m.p. |
|---|---|---|---|---|---|---|---|
| 193 | H | n-C₃H₇ | CO₂H | CH₂ | -N(CH₂CH(Ph)SCH₂CH₂) morpholine-thio with Ph | tetrazol-5-yl | |
| 194 | H | n-C₃H₇ | CO₂H | CH₂ | thiomorpholine-2,6-diMe | tetrazol-5-yl | |
| 195 | H | n-C₃H₇ | CO₂H | CH₂ | thiomorpholine-S,S-dioxide | tetrazol-5-yl | |
| 196 | H | n-C₃H₇ | CO₂H | CH₂ | 3-Ph-thiomorpholine-1,1-dioxide | tetrazol-5-yl | |
| 197 | H | n-C₃H₇ | CO₂H | CH₂ | 4-phenyl-piperazin-2-one | tetrazol-5-yl | |
| 198 | H | n-C₃H₇ | CO₂H | CH₂ | 4-phenyl-piperazin-3-one | tetrazol-5-yl | |
| 199 | H | n-C₃H₇ | CO₂H | CH₂ | 4-phenyl-piperazine-2,5-dione | tetrazol-5-yl | |
| 200 | H | n-C₃H₇ | CO₂H | CH₂ | 4-phenyl-piperazine-2,3-dione | tetrazol-5-yl | |

TABLE 2-continued

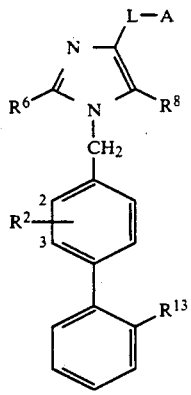

| Ex. No. | R² | R⁶ | R⁸ | L | A | R¹³ | m.p. |
|---|---|---|---|---|---|---|---|
| 201 | H | n-C₃H₇ | CO₂H | CH₂ | -N(C(=O)CH₂)₂N-Ph (2,6-dioxopiperazinyl-N-Ph) | tetrazol-5-yl | |
| 202 | H | n-C₃H₇ | CO₂H | CH₂ | -N(CH₂C(=O))₂N-Ph (2,5-dioxopiperazinyl-N-Ph) | tetrazol-5-yl | |
| 203 | H | n-C₃H₇ | CO₂H | CH₂ | -N-(3-oxo)-NCH₂Ph piperazine | tetrazol-5-yl | |
| 204 | H | n-C₃H₇ | CO₂H | CH₂ | -N-(2-oxo)-NCH₂Ph piperazine | tetrazol-5-yl | |
| 205 | H | n-C₃H₇ | CO₂H | CH₂ | -N-(3-oxo)-N-n-Bu piperazine | tetrazol-5-yl | |
| 206 | H | n-C₃H₇ | CO₂H | CH₂ | -N-(2-oxo)-N-n-Bu piperazine | tetrazol-5-yl | |
| 207 | H | n-C₃H₇ | CO₂H | CH₂ | -N-(3-methyl-2-oxo)-N-Ph piperazine | tetrazol-5-yl | |

TABLE 2-continued

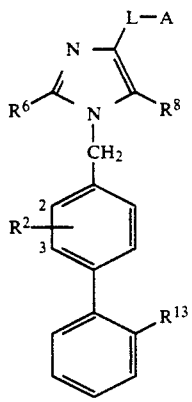

| Ex. No. | R² | R⁶ | R⁸ | L | A | R¹³ | m.p. |
|---|---|---|---|---|---|---|---|
| 208 | H | n-C₃H₇ | CO₂H | CH₂ | −N(CH(CH₃))C(=O)N(CH₂Ph)CH₂CH₂− (piperazinone, 3-CH₃, 4-NCH₂Ph) | tetrazol-5-yl | |
| 209 | H | n-C₃H₇ | CO₂H | CH₂ | −N(CH(CH₃))C(=O)N(n-Bu)CH₂CH₂− | tetrazol-5-yl | |
| 210 | H | n-C₃H₇ | CO₂H | CH₂ | −N(CH(n-C₅H₁₁))C(=O)N(Ph)CH₂CH₂− | tetrazol-5-yl | |
| 211 | H | n-C₃H₇ | CO₂H | CH₂ | −N(CH(n-C₅H₁₁))C(=O)N(CH₂Ph)CH₂CH₂− | tetrazol-5-yl | |
| 212 | H | n-C₃H₇ | CO₂H | CH₂ | −N(CH(n-C₅H₁₁))C(=O)N(n-Bu)CH₂CH₂− | tetrazol-5-yl | |
| 213 | H | n-C₃H₇ | CO₂H | CH₂ | −N(CH(PhCH₂))C(=O)N(Ph)CH₂CH₂− | tetrazol-5-yl | |
| 214 | H | n-C₃H₇ | CO₂H | CH₂ | −N(CH(PhCH₂))C(=O)N(CH₂Ph)CH₂CH₂− | tetrazol-5-yl | |

TABLE 2-continued

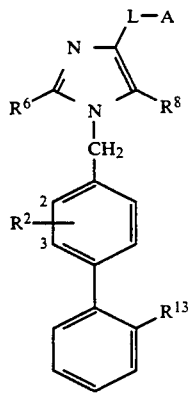

| Ex. No. | R² | R⁶ | R⁸ | L | A | R¹³ | m.p. |
|---|---|---|---|---|---|---|---|
| 215 | H | n-C₃H₇ | CO₂H | CH₂ | —N(piperazinone, N'-n-Bu, PhCH₂) | tetrazol-5-yl | |
| 216 | H | n-C₃H₇ | CO₂H | CH₂ | —N(piperazinone, N'-2-pyridyl, PhCH₂) | tetrazol-5-yl | |
| 217 | H | n-C₃H₇ | CO₂H | CH₂ | —N(piperazinone, N'-Ph, Ph) | tetrazol-5-yl | |
| 218 | H | n-C₃H₇ | CO₂H | CH₂ | —N(piperazinone, N'-CH₂Ph, Ph) | tetrazol-5-yl | |
| 219 | H | n-C₃H₇ | CO₂H | CH₂ | —N(piperazinone, N'-n-Bu, Ph) | tetrazol-5-yl | |
| 220 | H | n-C₃H₇ | CO₂H | CH₂ | —N(piperazinone, N'-Ph, n-Bu) | tetrazol-5-yl | |
| 221 | H | n-C₃H₇ | CO₂H | CH₂ | —N(piperazinone, N'-CH₂Ph, n-Bu) | tetrazol-5-yl | |

TABLE 2-continued

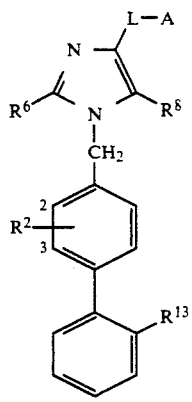

| Ex. No. | R² | R⁶ | R⁸ | L | A | R¹³ | m.p. |
|---|---|---|---|---|---|---|---|
| 222 | H | n-C₃H₇ | CO₂H | CH₂ | —N(CH₂CH₂)N-n-Bu with n-Bu and O substituents | tetrazol-5-yl | |
| 223 | H | n-C₃H₇ | CO₂H | CH₂ | piperazinone with N-phenyl and CH₃ | tetrazol-5-yl | |
| 224 | H | n-C₃H₇ | CO₂H | CH₂ | piperazinone with NCH₂Ph and CH₃ | tetrazol-5-yl | |
| 225 | H | n-C₃H₇ | CO₂H | CH₂ | piperazinone with N-n-Bu and CH₃ | tetrazol-5-yl | |
| 226 | H | n-C₃H₇ | CO₂H | CH₂ | piperazinone with N-phenyl and n-Bu | tetrazol-5-yl | |
| 227 | H | n-C₃H₇ | CO₂H | CH₂ | piperazinone with NCH₂Ph and n-Bu | tetrazol-5-yl | |
| 228 | H | n-C₃H₇ | CO₂H | CH₂ | piperazinone with N-n-Bu and n-Bu | tetrazol-5-yl | |

TABLE 2-continued

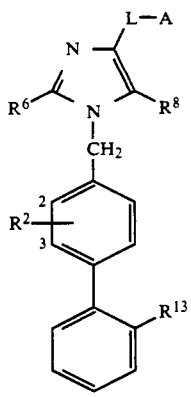

| Ex. No. | R² | R⁶ | R⁸ | L | A | R¹³ | m.p. |
|---|---|---|---|---|---|---|---|
| 229 | H | n-C₃H₇ | CO₂H | CH₂ | −N(piperazin-2-one, 4-Ph, 3-n-C₅H₁₁) | tetrazol-5-yl | |
| 230 | H | n-C₃H₇ | CO₂H | CH₂ | −N(piperazin-2-one, 4-NCH₂Ph, 3-n-C₅H₁₁) | tetrazol-5-yl | |
| 231 | H | n-C₃H₇ | CO₂H | CH₂ | −N(piperazin-2-one, 4-N-n-Bu, 3-n-C₅H₁₁) | tetrazol-5-yl | |
| 232 | H | n-C₃H₇ | CO₂H | CH₂ | −N(piperazin-2-one, 4-Ph, 3-CH₂Ph) | tetrazol-5-yl | |
| 233 | H | n-C₃H₇ | CO₂H | CH₂ | −N(piperazin-2-one, 4-NCH₂Ph, 3-CH₂Ph) | tetrazol-5-yl | |
| 234 | H | n-C₃H₇ | CO₂H | CH₂ | −N(piperazin-2-one, 4-N-n-Bu, 3-CH₂Ph) | tetrazol-5-yl | |
| 235 | H | C₃H₇ | CO₂H | CH₂ | −N(piperazin-2-one, 4-Ph, 3-Ph) | tetrazol-5-yl | |

TABLE 2-continued

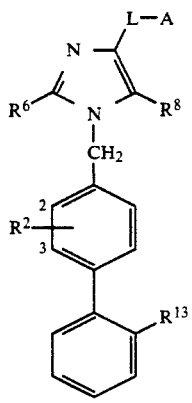

| Ex. No. | R² | R⁶ | R⁸ | L | A | R¹³ | m.p. |
|---|---|---|---|---|---|---|---|
| 236 | H | n-C₃H₇ | CO₂H | CH₂ | −N(CH₂CH₂)NCH₂Ph, C(=O), Ph | tetrazol-5-yl | |
| 237 | H | n-C₃H₇ | CO₂H | CH₂ | −N(CH₂CH₂)N-n-Bu, C(=O), Ph | tetrazol-5-yl | |
| 238 | H | n-C₃H₇ | CO₂H | CH₂ | −N−CH(Ph)−C(=O)−N(Ph)−CH₂−C(=O)− | tetrazol-5-yl | |
| 239 | H | n-C₃H₇ | CO₂H | CH₂ | −N−CH₂−C(=O)−N(Ph)−CH(Ph)−C(=O)− | tetrazol-5-yl | |
| 240 | H | n-C₃H₇ | CO₂H | CH₂ | −N−CH(Ph)−C(=O)−N(Ph)−CH(CH₃)−C(=O)− | tetrazol-5-yl | |
| 241 | H | n-C₃H₇ | CO₂H | CH₂ | −N−C(=O)−C(=O)−N(Ph)−CH₂−CH(Ph)− | tetrazol-5-yl | |
| 242 | H | n-C₃H₇ | CO₂H | CH₂ | −N−CH₂−C(=O)−N(Ph)−CH(Ph)−C(=O)− | tetrazol-5-yl | |

| Ex. No. | R² | R⁶ | R⁸ | L | A | R¹³ | m.p. |
|---|---|---|---|---|---|---|---|
| 243 | H | n-C₃H₇ | CO₂H | CH₂ | (structure: -N-CH(Ph)-C(=O)-N(Ph)-CH₂-C(=O)- ring) | tetrazol-5-yl | |
| 244 | H | n-C₃H₇ | CO₂H | CH₂ | (structure: -N-CH(CH(CH₃)₂)-CH₂-O-CH(CH₃)-C(=O)- ring) | tetrazol-5-yl | |
| 245 | H | n-C₃H₇ | CO₂H | CH₂ | (structure: -N-CH₂-S-CH(Ph)-C(=O)- ring) | tetrazol-5-yl | |
| 246 | H | n-C₃H₇ | CO₂H | CH₂ | (structure: -N-CH(CH(CH₃)₂)-CH₂-S-CH(CH₃)-C(=O)- ring) | tetrazol-5-yl | |

Footnotes for Table 2 a. See Experimental Section.

b. ¹H NMR (300MHz, DMSO-d₆): δ0.85(t, J=7.3Hz, 3H); 1.58(m, 2H); 2.60(t, 2H); 2.80(br. s, 4H); 3.56(br. s, 4H); 4.02(s, 2H, CH₂-piperazine); 5.60(s, 2H, benzyl); 6.64(m, 1H); 6.84(m, 1H); 7.02(m, 4H); 7.51-7.69(m, 5H); 8.11(m, 1H); 9.96(s, 1H, CHO). MS (NH₃-DCI): m/z 548(M+H); 387(M+H-pyridylpiperazine); 164(pyridylpiperazine+H). IR (KBr) 1710 cm⁻¹.

c. ¹H NMR (300MHz, DMSO-d₆): δ0.84(t, J=7.3Hz, 3H); 1.54(m, 2H); 2.46(t); 2.98(br. s, 4H); 3.66(br. s, 4H); 3.92(s, 2H); 4.42(s, 2H); 5.25(s, 2H); 6.66-8.13(m, 12H). MS (NH₃-DCI): m/z 550(M+H); 164(pyridylpiperazine+H). IR (KBr) 3310 cm⁻¹ (br.).

d. ¹H NMR (300MHz, DMSO-d₆): δ0.86(t, J=7.3Hz, 3H); 1.58(m, 2H); 2.53(t); 3.10(br. s, 4H); 3.69(br. s, 4H); 4.23(s, 2H, CH₂-piperazine); 5.72(s, 2H); 6.50-7.06(m, 5H); 7.55-7.70(m, 5H); 8.14(d, J=3.7Hz, 1H). MS (NH₃-DCI): m/z 582(M+H); 538(M+H - CO₂); 164(pyridylpiperazine+ H).

e. ¹H NMR (300MHz, DMSO-d₆): δ1.10(t, 3H, J=7.3Hz); 2.56(q, 2H, J=7.3Hz); 3.15(br. s, 4H); 3.70(br. s, 4H); 4.28(s, 2H); 5.68(s, 2H); 6.72-8.16(m, 12H). MS (NH₃-DCI): m/z 550(M+H); 506(M+H - CO₂). Calculated mass for C₃₀H₃₂N₉O₂ (M+H): 550.267897; found: 550.268938.

f. ¹H NMR (300MHz, DMSO-d₆): δ0.84(t, J=7.3Hz, 3H); 0.97(d, J=6.6Hz, 3H); 1.56(m, 2H); 2.25(s, 3H); 2.46(m); 2.78(m, 1H); 3.00(m,); 3.15(m, 1H); 3.40(m, 2H); 4.07(br. s+sh., 3H); 5.69(ABq, J=16Hz, 2H, benzyl); 6.64(d, J=7.0Hz, 1H); 6.73(m, 2H); 6.90(d, J=7.7Hz, 2H); 7.04(d, J=8.1Hz, 2H); 7.12(t, J=7.7Hz, 1H); 7.49(m, 2H); 7.59(m, 2H). MS (NH₃-DCI): m/z 591(M+H); 547(M+H - CO₂).

g. ¹H NMR (300MHz, DMSO-d₆): δ0.85(t, J=7.3Hz, 3H); 1.10(d, J=6.2Hz, 6H); 1.57(m, 2H); 2.33(t, J=11Hz, 2H, CH—N, morpholine); 2.48(t); 3.06(d, J=11Hz, 2H, CH—N, morpholine); 3.65(m, 2H); 4.03(s, 2H, CH₂—N); 5.71(s, 2H, benzyl); 6.48(t, J=7.8Hz, 1H); 6.80(d, J=7.6Hz, 1H); 7.00(d, J=11Hz, 1H); 7.52-7.69(m, 4H). MS (NH₃-DCI): m/z 534(M+H); 490(M+H - CO₂); 420(M+H-dimethylmorpholine); 116(dimethylmorpholine+H).

h. ¹H NMR (300MHz, DMSO-d₆): δ0.84(t, J=7.3Hz, 3H); 1.55(m, 2H); 2.54(t); 2.91(br. s, 4H); 3.31(br. s, 4H); 4.30(s, 2H, CH₂—N); 5.65(s, 2H, benzyl); 6.95-7.07(m, 4H); 7.57-7.70(m, 4H). MS (NH₃-DCI): m/z 504(M+H); 460(M+H - CO₂); 104(thiomorpholine+H).

i. ¹H NMR (300MHz, DMSO-d₆): δ0.84(t, J=7.3Hz, 3H); 1.57(m, 2H); 2.30(s, 3H); 2.46(t, obscured); 3.01(br. s, 4H); 3.64(br. s, 4H); 4.15(s, 2H, CH₂—N); 5.63(s, 2H, benzyl); 6.01(d, J=8.1Hz, 1H); 6.71(br. t, 2H); 6.90(d, J=8.4Hz, 1H); 7.03(s, 1H); 7.51-7.66(m, 5H); 8.14(m, 1H). MS (NH₃-DCI): m/z 578(M+H - CO₂); 164(pyridylpiperazine).

Utility

Angiotensin-II (AII) produces numerous biological responses (e.g. vasoconstriction) through stimulation of its receptors on cell membranes. For the purpose of identifying compounds such as AII antagonists which are capable of interacting with the AII receptor, a ligand-receptor binding assay was utilized for the initial screen. The assay was carried out according to the method described by [Chiu, et al., *Receptor*, 1 33, (1990)]. In brief, aliquots of a freshly prepared particulate fraction of rat adrenal cortex were incubated with 0.05 nM [$^{125}$I] AII and varying concentrations of potential AII antagonists in a Tris buffer. After a 1 h incubation the reaction was terminated by addition of cold assay buffer. The bound and free radioactivity were rapidly separated through glass-fiber filters, and the trapped radioactivity was quantitated by scintillation counting. The inhibitory concentration ($IC_{50}$) of potential AII antagonists which gives 50% displacement of the total specifically bound [$^{125}$I] AII is presented as a measure of the affinity of such compound for the AII receptor.

Using the assay method described above, the compounds of this invention are found to exhibit an activity of at least $IC_{50} < 10$ micromolar, thereby demonstrating and confirming the activity of these compounds as effective AII antagonists.

The potential antihypertensive effects of the compounds of this invention may be demonstrated by administering the compounds to awake rats made hypertensive by ligation of the left renal artery [Cangiano, et al., *J. Pharmacol. Exp. Ther.*, 1979, 208, 310]. This procedure increases blood pressure by increasing renin production with consequent elevation of AII levels. Compounds are administered intravenously via cannula in the jugular vein to give a cumulative dose of 10 mg/kg. Arterial blood pressure is continuously measured directly through a carotid artery cannula and recorded using a pressure transducer and a polygraph. Blood pressure levels after treatment are compared to pretreatment levels to determine the antihypertensive effects of the compounds.

Using the in vivo methodology described above, the compounds of this invention are found to exhibit an activity (intravenous) which is 10 mg/kg or less, and/or an activity (oral) which is 100 mg/kg or less, thereby demonstrating and confirming the utility of these compounds as effective agents in lowering blood pressure.

The compounds of the invention are useful in treating hypertension. They are also of value in the management of acute and chronic congestive heart failure and angina. These compounds may also be expected to be useful in the treatment of primary and secondary hyperaldosteronism; renal diseases such as diabetic nephropathy, glomerulonephritis, glomerular sclerosis, nephrotic syndrome, hypertensive nephrosclerosis, end stage renal disease, used in renal transplant therapy, and to treat renovascular hypertension, scleroderma, left ventricular dysfunction, systolic and diastolic dysfunction, diabetic retinopathy and in the management of vascular disorders such as migraine, Raynaud's disease, and as prophylaxis to minimize the atherosclerotic process and neointimal hyperplasia following angioplasty or vascular injury and to retard the onset of type II diabetes. The application of the compounds of this invention for these and similar disorders will be apparent to those skilled in the art.

The compounds of this invention are also useful to treat elevated intraocular pressure and to enhance retinal blood flow and can be administered to patients in need of such treatment with typical pharmaceutical formulations such as tablets, capsules, injectables and the like as well as topical ocular formulations in the form of solutions, ointments, inserts, gels and the like. Pharmaceutical formulations prepared to treat intraocular pressure would typically contain about 0.1% to 15% by weight, preferably 0.5% to 2% by weight, of a compound of this invention. For this use, the compounds of this invention may also be used in combination with other medications for the treatment of glaucoma including choline esterase inhibitors such as physostigmine salicylate or demecarium bromide, parasympathomimetic agents such as pilocarpine nitrate, $\beta$-adrenergic antagonists such as timolol maleate, adrenergic agonists such as epinephrine and carbonic anhydrase inhibitors such as MK-507.

In the management of hypertension and the clinical conditions noted above, the compounds of this invention may be utilized with a pharmaceutical carrier in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets being followed by a patient, concurrent medication, and other factors which those skilled in the art will recognize, the dosage range will generally be about 1 to 1000 mg per patient per day which can be administered in single or multiple doses. Preferably, the dosage range will be about 5 to 500 mg per patient per day; more preferably about 5 to 300 mg per patient per day.

The compounds of this invention can also be administered in combination with other antihypertensives and/or diuretics. For example, the compounds of this invention can be given in combination with diuretics such as hydrochlorothiazide, chlorothiazide, chlorthalidone, methylclothiazide, furosemide, ethacrynic acid, triamterene, amiloride spironolactone and atriopeptin; calcium channel blockers, such as diltiazem, felodipine, nifedipine, amlodipine, nimodipine, isradipine, nitrendipine and verapamil; $\beta$-adrenergic antagonists such as timolol, atenolol, metoprolol, propanolol, nadolol and pindolol; angiotensin converting enzyme inhibitors such as enalapril, lisinopril, captopril, ramipril, quinapril and zofenopril; renin inhibitors such as A-69729, FK 906 and FK 744; $\alpha$-adrenergic antagonists such as prazosin, doxazosin, and terazosin; sympatholytic agents such as methyldopa, clonidine and guanabenz; atriopeptidase inhibitors (alone or with ANP) such as UK-79300; serotonin antagonists such as ketanserin; $A_2$-adrenosine receptor agonists such as CGS 22492C; potassium channel agonists such as pinacidil and cromakalim; and various other antihypertensive drugs including reserpine, minoxidil, guanethidine, hydralazinc hydrochloride and sodium nitroprusside as well as combinations of the above-named drugs. Combinations useful in the management of congestive heart failure include, in addition, compounds of this invention with cardiac stimulants such as dobutamine and xamoterol and phosphodiesterase inhibitors including amrinone and milrinone.

Typically, the individual daily dosages for these combinations can range from about one-fifth of the minimally recommended clinical dosages to the maximum recommended levels for the entities when they are given singly. To illustrate these combinations, one of the angiotensin-II antagonists of this invention effective clinically in the 5–500 milligrams per day range can be effectively combined at levels at the 1.0–500 milligrams per day range with the following compounds at the indicated per day dose range: hydrochlorothiazide (6–100 mg), chlorothiazide (125–500 mg), ethacrynic acid (5–200 mg), amiloride (5–20 mg), furosemide (5–80 mg), propranolol (10–480 mg), timolol maleate (1–20 mg), methyldopa (125–2000 mg), felodipine (1–20 mg), nifedipine (5–120 mg), nitrendipine (5–60 mg), and diltiazem (30–540 mg). In addition, triple drug combinations of hydrochlorothiazide (5–100 mg) plus amiloride (5–20 mg) plus angiotensin-II antagonists of this invention (1–500 mg) or hydrochlorothiazide (5–100 mg) plus timolol maleate (5–60 mg) plus an angiotensin-II antagonists of this invention (1–500 mg) or hydrochlorothiazide (5–200 mg) and nifedipine (5–60 mg) plus an angiotensin-II antagonist of this invention (1–500 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

The active ingredient can be administered orally in solid dosage forms, such as capsules, tablets, and powders, or in liquid dosage forms, such as elixirs syrups, and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in *Remington's Pharmaceutical Sciences*, A. Osol, a standard reference text in this field.

Useful pharmaceutical dosage-forms for administration of the compounds of this invention can be illustrated as follows:

Capsules

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol. The solution is made to volume with water for injection and sterilized.

Suspension

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise in conjunction with another therapeutic agent. When the drugs are administered in physical combination, the dosage form and administration route should be selected for compatibility with both drugs.

What is claimed is:

1. A compound of Formula (I)

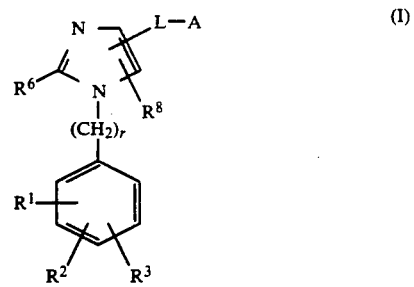

wherein
$R^1$ is in the meta or para position and is

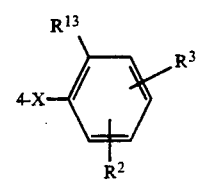

$R^2$ is independently
(a) H, (b) halo
(c) $C_1$-$C_4$ alkyl,
(d) $C_1$-$C_4$ alkoxy,
(e) $C_1$-$C_4$ acyloxy,
(f) $C_1$-$C_4$ alkylthio,
(g) $C_1$-$C_4$ alkylsulfinyl,
(h) $C_1$-$C_4$ alkylsulfonyl,
(i) hydroxy ($C_1$-$C_4$) alkyl,
(j) aryl ($C_1$-$C_4$) alkyl,
(k) —$CO_2H$,
(l) —CN,
(m) tetrazol-5-yl,
(n) —$CONHOR^{12}$,
(o) —$SO_2NHR^9$,
(p) —$NH_2$,
(q) $C_1$-$C_4$ alkylamino,
(r) $C_1$-$C_4$ dialkylamino,
(s) —$NHSO_2R^{10}$,
(t) —$NO_2$,
(u) furyl,
(v) aryl;

$R^3$ is independently
(a) H,
(b) halo,
(c) $C_1$-$C_4$ alkyl,
(d) $C_1$-$C_4$ alkoxy,
(e) $C_1$-$C_4$ alkoxyalkyl;

$R^5$ is
(a) H,
(b) $C_1$-$C_6$ alkyl,
(c) $C_3$-$C_6$ cycloalkyl,
(d) $C_2$-$C_4$ alkenyl,
(e) $C_2$-$C_4$ alkynyl;

$R^6$ is
(a) $C_1$-$C_{10}$ alkyl,
(b) $C_3$-$C_{10}$ alkenyl,
(c) $C_3$-$C_{10}$ alkynyl,
(d) $C_3$-$C_8$ cycloalkyl,
(e) $C_4$-$C_8$ cycloalkenyl,
(f) $C_4$-$C_{10}$ cycloalkylalkyl,
(g) $C_5$-$C_{10}$ cycloalkylalkenyl,
(h) $C_5$-$C_{10}$ cycloalkylalkynyl,
(i) —$(CH_2)_sZ^2(CH_2)_mR^5$,
(j) benzyl, optionally substituted on the phenyl ring with 1-2 substituents selected from the group consisting of halo, $C_1$-$C_4$ alkyl, $C_1$-$C_4$ alkoxy or —$NO_2$;

$R^8$ is
(a) H,
(b) $C_1$-$C_4$ alkyl,
(c) —$(CH_2)_nCHR^{34}OR^{29}$,
(d) —$COR^{35}$,
(e) —$(CH_2)_nCHR^{34}COR^{35}$,
(f) —$CR^{36}$=$CR^{37}COR^{35}$,
(g) —$CONHOR^{12}$;

$R^9$ is
(a) H,
(b) $C_1$-$C_5$ alkyl,
(c) aryl,
(d) —$CH_2$-aryl;

$R^{10}$ is
(a) aryl,
(b) $C_3$-$C_7$ cycloalkyl,
(c) $C_1$-$C_4$ perfluoroalkyl,
(d) $C_1$-$C_4$ alkyl optionally substituted with a substituent selected from the group consisting of aryl, —OH, —SH, $C_1$-$C_4$ alkyl, $C_1$-$C_4$ alkoxy, $C_1$-$C_4$ alkylthio, —$CF_3$, halo, —$NO_2$, —$CO_2H$, —$CO_2CH_3$, —$CO_2$-benzyl, —$NH_2$, $C_1$-$C_4$ alkylamino, $C_1$-$C_4$ adialkylamino, —$PO_3H_2$;

$R^{11}$ is
(a) H,
(b) $C_1$-$C_6$ alkyl,
(c) $C_3$-$C_6$ cycloalkyl,
(d) phenyl,
(e) benzyl;

$R^{12}$ is
(a) H,
(b) methyl,
(c) benzyl;

$R^{13}$ is

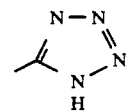

$R^{14}$ is
(a) H,
(b) $C_1$-$C_6$ alkyl,
(c) $CH_2CH$=$CH_2$,
(d) benzyl;

$R^{15}$ is
(a) H,
(b) $C_1$-$C_8$ alkyl,
(c) $C_1$-$C_8$ perfluoroalkyl,
(d) $C_3$-$C_6$ cycloalkyl,
(e) phenyl,
(f) benzyl;

$R^{16}$ is
(a) H,
(b) $C_1$-$C_6$ alkyl,
(c) benzyl;

$R^{17}$ is
(a) H,
(b) $C_1$-$C_6$ alkyl,
(c) $C_3$-$C_6$ cycloalkyl,
(d) phenyl,
(e) benzyl;

$R^{18}$ is
(a) —$NR^{19}R^{20}$—,
(b) —$NHCONH_2$,
(c) —$NHCSNH_2$,
(d) —$NHSO_2$—$C_6H_5$;

$R^{19}$ and $R^{20}$ are independently
(a) H,
(b) $C_1$-$C_5$ alkyl,
(c) phenyl, $R^{21}$ and $R^{22}$ are independently
(a) $C_1$-$C_4$ alkyl or taken together are
(b) —$(CH_2)_q$—;

L is a divalent group which is a
(a) $C_1$ to $C_8$ alkylene chain,
(b) $C_3$ to $C_8$ alkenylene chain,
(c) $C_3$ to $C_8$ alkynylene chain,
(d) $C_2$ to $C_8$ alkylene chain containing O,
(e) $C_2$ to $C_8$ alkenyl chain containing $S(O)_{0-2}$,
(f) $C_2$ to $C_8$ alkylene chain containing $NR^{23}$;
wherein the alkylene, alkenylene and alkynylene chains may be branched or unbranched, 0 to 1 carbon atoms of L may comprise a carbonyl group, and both termini of L comprise carbon atoms;

$R^{23}$ is
(a) H,
(b) $C_1$-$C_6$ alkyl, (c) $C_3$-$C_6$ alkenyl,
(d) aryl,
(e) aryl ($C_1$-$C_4$) alkyl,
(f) $C_2$-$C_6$ alkanoyl,
(g) arylcarbonyl,
(h) aryl ($C_1$-$C_4$) alkanoyl,
(i) $C_1$-$C_6$ alkoxycarbonyl;

A is a piperazine ring substituted by $R^{24}$ and $R^{25}$ and attached to L through nitrogen in which 0-2 ring carbons comprise carbonyl groups and N-4 is substituted by $R^{26}$ or $R^{28}$;

$R^{24}$ is
(a) H,
(b) $C_1$-$C_6$ alkyl,
(c) aryl,
(d) aryl ($C_1$-$C_4$) alkyl,
(e) diaryl ($C_1$-$C_4$) alkyl,
(f) —$OR^{29}$,
(g) —$(CH_2)_rCO_2R^{29}$,
(h) —$(CH_2)_rCH_2OR^{29}$,
(i) —$(CH_2)_rCONR^{31}R^{32}$,
(j) —$(CH_2)_rCH_2NR^{31}R^{32}$,
(k) —$(CH_2)_rCH_2SH$,
(l) —$(CH_2)_rCH_2S(O)_{0-2}R^{30}$,
(m) —$(CH_2)_5CH_2NHC(NH_2)=NH$;

$R^{25}$ is
(a) H,
(b) $C_1$-$C_6$ alkyl,
(c) aryl,
(d) aryl ($C_1$-$C_4$) alkyl;

$R^{26}$ is
(a) H,
(b) $C_3$-$C_6$ cycloalkyl,
(c) $C_4$-$C_8$ cycloalkylalkyl,
(d) aryl,
(e) pyridyl,
(f) aryl ($C_1$-$C_4$) alkyl,
(g) diaryl ($C_1$-$C_4$) alkyl,
(h) ($C_3$-$C_6$ cycloalkyl) aryl ($C_1$-$C_4$) alkyl,
(i) aryl ($C_3$-$C_6$) cycloalkyl,
(j) $C_2$-$C_8$ alkoxyalkyl;

$R^{28}$ is
(a) $C_1$-$C_6$ alkanoyl,
(b) arylcarbonyl,
(c) aryl ($C_1$-$C_4$) alkanoyl,
(d) diaryl ($C_1$-$C_4$) alkanoyl,
(e) —$CO_2R^{33}$,
(f) —$CONHR^{31}R^{32}$, $R^{29}$ is
(a) H,
(b) $C_1$-$C_6$ alkyl,
(c) aryl,
(d) aryl ($C_1$-$C_4$) alkyl,
(e) diaryl ($C_1$-$C_4$) alkyl;

$R^{30}$ is
(a) $C_1$-$C_6$ alkyl,
(b) aryl,
(c) aryl ($C_1$-$C_4$) alkyl,
(d) diaryl ($C_1$-$C_4$) alkyl;

$R^{31}$ and $R^{32}$ are, independently
(a) H,
(b) $C_1$-$C_6$ alkyl,
(c) aryl,
(d) aryl ($C_1$-$C_4$) alkyl;
or $R^{31}$ and $R^{32}$ when taken together constitute a pyrrolidine, piperidine or morpholine ring;

$R^{33}$ is
(a) $C_1$-$C_6$ alkyl,
(b) aryl,
(c) aryl ($C_1$-$C_4$) alkyl,
(d) diaryl ($C_1$-$C_4$) alkyl;

$R^{34}$ is
(a) H,
(b) $C_1$-$C_4$ alkyl,
(c) $C_3$-$C_6$ cycloalkyl,
(d) aryl,
(e) aryl ($C_1$-$C_4$) alkyl;

$R^{35}$ is
(a) H,
(b) $OR^{29}$,
(c) $NR^{38}R^{39}$;

$R^{36}$ and $R^{37}$ are independently
(a) H,
(b) $C_1$-$C_4$ alkyl,
(c) aryl,
(d) arylmethyl;

$R^{38}$ and $R^{39}$ are independently
(a) H,
(b) $C_1$-$C_4$ alkyl,
(c) aryl,
(d) arylmethyl,
or taken together comprise
(e) —$(CH_2)_u$—,
(f) a morpholine ring;

X is
(a) a carbon-carbon single bond,
(b) —CO—,
(c) —$C(R^{19})(R^{20})$—,
(d) —O—,
(e) —S—,
(f) —SO—,
(g) —$SO_2$—,
(h) —$NR^{14}$—,
(i) —$CONR^{16}$—,
(j) —$NR^{16}CO$—,
(k) —$OC(R^{19})(R^{20})$—,
(l) —$C(R^{19})(R^{20})O$—,
(m) —$SC(R^{19})(R^{20})$—,
(n) —$C(R^{19})(R^{20})S$—,
(o) —$NHC(R^{19})(R^{20})$—,
(p) —$C(R^{19})(R^{20})NH$—,
(q) —$NR^{16}SO_2$—,
(r) —$SO_2NR^{16}$—,
(s) —CH=CH—,
(t) —CF=CF—,
(u) —CF=CH—,
(v) —CF=CH—,
(w) —$CF_2CF_2$—,
(x) —$CH(OR^{15})$—,
(y) —$CH(OCOR^{17})$—,
(z) —$C(=NR^{18})$—,
(aa) —$C(OR^{21})(OR^{22})$—,
(bb) 1,2-cyclopropyl,
(cc) 1,1-cyclopropyl;

$Z^2$ is
(a) —O—,
(b) —S—,
(c) —$NR^{11}$—;

m is 1 to 5;
n is 0 to 2;
q is 2 to 3;
r is 0 to 2;
s is 0 to 5;
t is 0 to 3;
u is 2 to 5;

wherein aryl is phenyl optionally substituted with one or two substituents selected from the group consisting of halo, $C_1$-$C_4$ alkyl, $C_1$-$C_4$ alkoxy, $-NO_2$, $-CF_3$, $C_1$-$C_4$ alkylthio, $-OH$, $-NH_2$, $C_1$-$C_4$ alkylamino, $C_1$-$C_4$ dialkylamino, $-CN$, $-CO_2H$, $-CO_2CH_3$, $-CO_2CH_2CH_3$, $-CO_2$-benzyl, acetyl; and pharmaceutically acceptable salts of these compounds;

provided that when A is piperazine and $R^{24}$ and $R^{25}$ are both H then $R^{26}$ is not H, phenyl or $C_1$-$C_4$ alkoxyphenyl.

2. A compound of claim 1 wherein the L-A group on Formula (I) is in the 4-position and the $R^8$ group on Formula (I) is in the 5-position and wherein $R^6$ is
- (a) $C_1$-$C_{10}$ alkyl,
- (b) $C_3$-$C_{10}$ alkenyl,
- (c) $C_3$-$C_{10}$ alkynyl,
- (d) $C_3$-$C_8$ cycloalkyl,
- (e) benzyl, optionally substituted on the phenyl ring with one or two substituents selected from the group consisting of halo, $C_1$-$C_4$ alkyl, $C_1$-$C_4$ alkoxy and $-NO_2$;

$R^{24}$ is
- (a) H,
- (b) $C_1$-$C_6$ alkyl,
- (c) aryl,
- (d) arylmethyl,
- (e) diarylmethyl,
- (f) $-(CH_2)_tCO_2R^{29}$,
- (g) $-(CH_2)_tCH_2OR^{29}$,
- (h) $-(CH_2)_tCONR^{31}R^{32}$,
- (i) $-(CH_2)_tCH_2NR^{31}R^{32}$,
- (j) $-(CH_2)_tCH_2SH$,
- (k) $-(CH_2)_tCH_2S(O)_{0-2}R^{30}$,
- (l) $-(CH_2)_tCH_2NHC(NH_2=NH$;

$R^{25}$ is
- (a) H,
- (b) $C_1$-$C_6$ alkyl,
- (c) aryl,
- (d) arylmethyl;

$R^{26}$ is
- (a) H,
- (b) $C_3$-$C_6$ cycloalkyl,
- (c) $C_4$-$C_8$ cycloalkylalkyl,
- (d) aryl,
- (e) pyridyl,
- (f) arylmethyl,
- (g) diarylmethyl,
- (h) aryl($C_3$-$C_6$cycloalkyl)methyl,
- (i) aryl ($C_3$-$C_6$) cycloalkyl,
- (j) $C_2$-$C_4$ alkoxyalkyl;

$R^{28}$ is
- (a) $C_1$-$C_6$ alkanoyl,
- (b) arylacetyl,
- (c) diarylacetyl,
- (d) $-CO_2R^{33}$,
- (e) $-CONR^{31}R^{32}$;

$R^{29}$ is
- (a) H,
- (b) $C_1$-$C_4$ alkyl,
- (c) aryl,
- (d) arylmethyl,
- (e) diarylmethyl;

$R^{30}$ is
- (a) $C_1$-$C_4$ alkyl,
- (b) aryl,
- (c) arylmethyl,
- (d) diarylmethyl;

$R^{31}$ and $R^{32}$ are, independently
- (a) H,
- (b) $C_1$-$C_4$ alkyl,
- (c) aryl,
- (d) arylmethyl;

or $R^{31}$ and $R^{32}$ when taken together constitute a morpholine ring;

$R^{33}$ is
- (a) $C_1$-$C_4$ alkyl,
- (b) aryl,
- (c) arylmethyl, $R^{34}$ is
- (a) H,
- (b) $C_1$-$C_4$ alkyl,
- (c) aryl,
- (d) arylmethyl;

$R^{38}$ and $R^{39}$ are independently
- (a) H,
- (b) $C_1$-$C_4$ alkyl,
- (c) aryl,
- (d) arylmethyl, or taken together comprise
- (e) a piperidine ring,
- (f) a morpholine ring;

X is
- (a) a carbon-carbon single bond,
- (b) $-CO-$,
- (c) $-O-$,
- (d) $-S-$,
- (e) $-CONR^{16}-$,
- (f) $-NR^{16}CO-$,
- (g) $-OCH_2-$,
- (h) $-CH_2O-$,
- (h) $-SCH_2-$,
- (j) $-CH_2S-$,
- (k) $-NHCH_2-$,
- (l) $-CH_2NH-$,
- (m) $-CH=CH-$, n is 0;

t is 0 to 2;

where aryl at each occurrence is as defined in claim 1; and pharmaceutically acceptable salts.

3. A compound of claim 2, wherein $R^2$ and $R^3$ are independently
- (a) H,
- (b) halo,
- (c) $C_1$-$C_4$ alkyl,
- (d) $C_1$-$C_4$ alkoxy;

$R^6$ is
- (a) $C_2$-$C_7$ alkyl,
- (b) $C_3$-$C_6$ alkenyl,
- (c) $C_3$-$C_6$ alkynyl;

$R^{25}$ is H;

$R^{26}$ is
- (a) H,
- (b) $C_3$-$C_6$ cycloalkyl,
- (c) aryl,
- (d) pyridyl,
- (e) arylmethyl,
- (f) heteroarylmethyl, $R^{30}$ is
- (a) $C_1$-$C_4$ alkyl,
- (b) aryl,
- (c) arylmethyl, $R^{34}$ is H;

$R^{36}$ and $R^{37}$ are H;

X is
- (a) a carbon-carbon single bond, (b) —O—,
(c) —CO—,
(d) —NHCO—,
(e) —OCH$_2$;

where aryl at each occurrence is as defined in claim 1; and pharmaceutically acceptable salts.

4. A compound of claim 3 wherein
R$^{24}$ is
(a) H,
(b) C$_1$-C$_6$ alkyl,
(c) aryl,
(d) arylmethyl,
R$^{26}$ is
(a) H,
(b) aryl,
(c) arylmethyl,
R$^{35}$ is
(a) H,
(b) —OR$^{29}$,
X is a carbon-carbon single bond;
where aryl at each occurrence is as defined in claim and pharmaceutically acceptable salts.

5. A compound of claim 4 selected from the group consisting of

5-Carboxy-4-[4-(2-pyridyl)-piperazin-1-yl]methyl-2-propyl-1-[(2'-tetrazol-5-yl)biphen-4-yl)methyl]-imidazole;

5-Carboxy-4-[4-(2-pyridyl)-piperazin-1-yl]methyl-2-propyl-1-[(2-fluoro-2'-(tetrazol-5-yl)biphen-4-yl)methyl]-imidazole;

4-[4-(2-Pyridyl)-piperazin-1-yl]methyl-2-propyl-1-[(2'-(tetrazol-5-yl)biphen-4-yl)methyl]-imidazole-5-carboxaldehyde;

5-Carboxy-4-[4-(2-pyridyl)-piperazin-1-yl]carbonyl-2-propyl-1-[(2'-tetrazol-5-yl)biphen-4-yl)methyl]-imidazole;

5-Carboxy-4-[4-(4-acetyl)phenylpiperazin-1-yl]methyl-2-propyl-1-[(2'-(tetrazol-5-yl)biphen-4-yl)methyl]-imidazole;

5-Carboxy-4-[4-(2-chlorophenyl )phenylpiperazin-1-yl]methyl-2-propyl-1-[(2'-(tetrazol-5-yl)biphen-4-yl)methyl]-imidazole;

5-Carboxy-4-[4-(3-trifluoromethylphenyl)-piperazin-1-yl]methyl-2-propyl-1-[(2'-(tetrazol-5-yl)biphen-4-yl)methyl]-imidazole;

5-Carboxy-4-(4-benzylpiperazin-1-yl)methyl-2propyl-1-[(2'-(tetrazol-5-yl)biphen-4-yl)methyl]-imidazole;

5-Carboxy-4-[4-(2-trifluoromethylbenzyl)-piperazin-1-yl]methyl-2-propyl-1-[(2'-(tetrazol-5-yl)biphen-4-yl)methyl]-imidazole.

6. A pharmaceutical composition comprising a pharmaceutically suitable carrier and an effective amount of a compound of any one of claims 1 through 4.

7. A pharmaceutical composition comprising a pharmaceutically suitable carrier and an effective amount of a compound of claim 5.

8. A method of treating hypertension in a warm blooded animal comprising administering to an animal in need of such treatment an effective amount of a compound of any one of claims 1 through 4.

9. A method of treating hypertension in a warm blooded animal comprising administering to an animal in need of such treatment an effective amount of a compound of claim 5.

10. A method of treating congestive heart failure in a warm blooded animal comprising administering to an animal in need of such treatment an effective amount of a compound of any one of claims 1 through 4.

11. A method of treating congestive heart failure in a warm blooded animal comprising administering to an animal in need of such treatment an effective amount of a compound of claim 5.

* * * * *